(12) United States Patent
Summar et al.

(10) Patent No.: US 10,525,026 B2
(45) Date of Patent: *Jan. 7, 2020

(54) INTRAVENOUS ADMINISTRATION OF CITRULLINE DURING SURGERY

(71) Applicant: Vanderbilt University, Nashville, TN (US)

(72) Inventors: Marshall L. Summar, Washington, DC (US); Frederick E. Barr, Ridgeland, MS (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/197,209

(22) Filed: Jun. 29, 2016

(65) Prior Publication Data

US 2016/0374972 A1 Dec. 29, 2016

Related U.S. Application Data

(60) Provisional application No. 62/186,085, filed on Jun. 29, 2015.

(51) Int. Cl.
| | |
|---|---|
| *A61K 9/00* | (2006.01) |
| *A61M 1/36* | (2006.01) |
| *A61P 9/00* | (2006.01) |
| *A61K 31/198* | (2006.01) |

(52) U.S. Cl.
CPC .......... *A61K 31/198* (2013.01); *A61K 9/0019* (2013.01); *A61M 1/3666* (2013.01); *A61P 9/00* (2018.01)

(58) Field of Classification Search
CPC .. A61K 31/198; A61K 9/0019; A61M 1/3666
See application file for complete search history.

(56) References Cited

U.S. PATENT DOCUMENTS

| 6,346,382 B1 | 2/2002 | Summar et al. |
|---|---|---|
| 6,743,823 B1 | 6/2004 | Summar et al. |
| 8,188,147 B2 | 5/2012 | Summar et al. |
| 8,536,225 B2 | 9/2013 | Summar et al. |
| 2004/0235953 A1 | 11/2004 | Summar et al. |
| 2008/0234379 A1 | 9/2008 | Summar et al. |
| 2009/0312423 A1 | 12/2009 | Summar et al. |
| 2012/0088835 A1 | 4/2012 | Summar et al. |
| 2012/0252895 A1 | 10/2012 | Summar et al. |

FOREIGN PATENT DOCUMENTS

| WO | WO 00/73322 | 12/2000 |
|---|---|---|
| WO | WO 2005/082042 | 9/2005 |
| WO | WO 2009/09998 | 8/2009 |
| WO | WO 2009/09999 | 8/2009 |

OTHER PUBLICATIONS

Clinicaltrials (Intravenous L-Citrulline to treat children undergoing Heart Bypass Surgery: Revised Protocol, NCT01120964, First posted, May 11 2010), (Year: 2010).*
Barr et al. *The J Pediatr* 142(1): 26-30, 2003.
Barr et al. *J Thoracic Cardiovasc Surgery* 134(2): 319-326, 2007.
Barr et al. Intravenous L-Citrulline to treat Children undergoing Heart Bypass Surgery: Revised Protocol. U.S. National Institutes of Health. Clinical Trial Report. [Retrieved on-line Aug. 16, 2016] (NTC01120964).
Burke et al. *Congenital Heart Disease* 27(3): 696-699, 1996.
Smith et al. *J Thoracic Cardiovasc Surgery* 132(1): 58-65, 2006.
Tobias et al. *Anesthesia & Analgesia* 88(3): 531-534, 1999.
International Search Report and Written Opinion for International Patent Application No. PCT/US2016/040138, dated Sep. 23, 2016.
Dagenais, Caroline et al., "Acute L-arginine supplement and cardiac surgery," Canadian Journal of Anaesthesia/Journal Canadien D'Anesthesie, vol. 43, No. 5 (2) p. A16 (2011) XP002422419, ISSN: 0832-610X.

\* cited by examiner

*Primary Examiner* — Umamaheswari Ramachandran
(74) *Attorney, Agent, or Firm* — Hunton Andrews Kurth LLP

(57) ABSTRACT

A method for administering citrulline to a patient during surgery without filtration of the hemolysis.

13 Claims, 18 Drawing Sheets

PK Model

PK Parameters

| Dose (mg/kg) | $R_{app}$ (μmol/hr/kg) | $K_{rem}$ (hr$^{-1}$) | $V_d$ (L/kg) |
|---|---|---|---|
| 50 | 21.3 | 0.69 | 1.36 |
| 100 | 22.3 | 0.69 | 1.44 |
| 150 | 20.1 | 0.72 | 1.17 |

INTRAVENOUS ADMINISTRATION OF CITRULLINE DURING SURGERY

CROSS-REFERENCE TO RELATED PATENT APPLICATIONS

This patent application claims priority to U.S. Provisional Patent Application No. 62/186,085, filed Jun. 29, 2015, the disclosure of which is incorporated herein in its entirety.

FIELD OF THE INVENTION

The present invention relates generally to the field of the maintaining pulmonary vascular tone in patients during surgery and postoperatively.

BACKGROUND OF THE INVENTION

Nitric Oxide

Endogenous nitric oxide (NO) plays a role in the regulation of pulmonary vascular tone. Nelin, et al. *Pediatr Res* (1994) 35: 20-24; Lipsitz, et al. *J Pediatr Surg* (1996) 31: 137-140. Nitric oxide is synthesized by different isoforms of the enzyme nitric oxide synthase (NOS). Endothelial NOS (eNOS) is a constitutive enzyme responsible for the calcium-calmodulin dependent production of baseline levels of NO. Inducible NOS (iNOS) catalyzes the calcium-independent production of large amounts of NO in response to certain cytokines and inflammatory stimuli. A third form of NOS is neuronal NOS (nNOS) serves as a neurotransmitter in both the central and peripheral nervous systems. Endothelial cells generate endogenous NO from arginine. Palmer, et al. *Biochem Biophys Res Commun* (1988) 153: 1251-6; Moncada, et al. *N Engl J Med* (1993) 329: 2002-12.

The hepatic urea cycle plays a role in the production of two precursors of nitric oxide: arginine and citrulline. Pearson, et al. *New England Journal of Medicine* (2001) 344: 1832-1838. The first two steps of the hepatic urea cycle, carried out by carbamyl phosphate synthetase I (CPSI) and ornithine transcarbamylase (OTC), produce citrulline. These two enzymes are located in mitochondria of the liver and gut with the remainder of the pathway distributed throughout the body, including the pulmonary vascular endothelium. Summar *J Inher Metab Dis* (1988) 21(S1): 30-39. Citrulline, an amino acid, is the first intermediate of the urea cycle. After citrulline is transported intracellularly via a selective membrane transporter, it is rapidly converted to arginine by the enzymes argininosuccinate synthetase (AS) and argininosuccinate lyase (AL).

After the rate limiting reaction catalyzed by CPSI, three other urea cycle enzymes participate in arginine formation (FIG. 1). In the next urea cycle step, ornithine transcarbamylase (OTC) combines carabamyl phosphate and ornithine to form citrulline. Citrulline is transported from the mitochondria to the cytoplasm. Argininosuccinate synthetase (AS) is the first of the cytoplasmic urea cycle enzymes and combines citrulline with aspartate to form argininosuccinate. See FIG. 1. Argininosuccinate lyase (AL) cleaves fumarate off of argininosuccinate to form arginine. See FIG. 1.

Citrulline and the Urea Cycle

The urea cycle enzymes argininosuccinic acid synthetase (AS) and argininosuccinic acid lyase (AL) participate in the NO regeneration pathway in endothelial tissues (FIG. 1). The substrate supply for this NO pathway comes from the production of citrulline as part of normal urea cycle function.

Arginine is a basic amino acid synthesized predominantly by the urea cycle (FIG. 1). Intracellular concentrations of arginine are many times greater that circulating plasma concentrations, yet NOS function appears to be regulated by plasma concentrations of arginine. Current theory proposes that this phenomenon is due to intracellular co-localization of the arginine transporter, CAT-1, and eNOS in the plasma membrane. CAT-1 uptake of plasma arginine is directly channeled into NO synthesis via eNOS while intracellular arginine stores are separately compartmentalized and unavailable. Both arginine and citrulline can be given orally, however the gut has a partially intact urea cycle and arginase converts much of the dietary arginine to urea. In normal volunteers, oral L-citrulline increases circulating arginine concentrations more than oral arginine.

Human CPSI (carbamoyl phosphate synthetase I) is the rate-limiting enzyme catalyzing the first committed step of ureagenesis in the hepatic urea cycle (FIG. 1). This cycle comprises the body's system for removing waste nitrogen produced by the metabolism of endogenous and exogenous protein. CPSI is highly tissue-specific, with function and production located in the liver and intestine. The product of a nuclear gene, CPSI is synthesized in the cytoplasm and transported into the mitochondria where it is cleaved into its mature 160 kDA monomeric form. The enzyme combines ammonia and bicarbonate to carbamyl phosphate with the expenditure of 2 ATPs and the necessary cofactor n-acetylglutamate (NAG). Rubio, et al. *Biochemistry* (1981) 20: 1969-1974; Rubio, et al. *Biochemica Biophysica Acta* (1981) 659: 150-160. Mature CPSI is modular in nature, containing 2 main regions. Of particular note is the NAG cofactor-binding domain near the carboxy-terminus of the enzyme. Without NAG binding the enzyme remains inert resulting in hyperammonemia and no citrulline production.

Over 60 CPSI mutations result in disruption of enzyme function. Summar *J Inher Metab Dis* (1988) 21(S1): 30-39. A common polymorphism is near the 3' end of the CPSI mRNA (45% heterozygosity). Sequence analysis of this change reveals a C to A transversion at base 4332, changing the triplet code from ACC to AAC. This results in a substitution of asparagine for threonine at amino acid 1405 (referred to as T1405N). The T1405N genotype is associated with pulmonary hypertension, a risk of elevated pulmonary vascular tone in infants and children undergoing correction of their congenital heart defects, and persistent pulmonary hypertension in the newborn (PPHN). Pearson, et al. *N Engl J Med* (2001) 344(24): 1832-8; Canter, et al. *Mitochondrion* (2007) 7(3): 204-10.

When arginine and citrulline values were examined in relation to the T1405N alleles, infants with the CC genotype had lower mean arginine and citrulline levels than infants with the AA genotype. Only the arginine values reached statistical significance with a p-value of 0.011. Heterozygous infants (AC genotype) had intermediate levels of arginine and citrulline, which were not statistically different from those of either homozygous group. See FIG. 2

CPSI is the rate-limiting step in the urea cycle, but polymorphisms in other urea cycle enzymes may also affect urea cycle flux and arginine availability. For example, polymorphisms in the enzymes OTC, AS, AL, and eNOS both separately and in combination with CPSI T1405N may have an effect on the postoperative pulmonary vascular tone in infants and children undergoing congenital heart surgery.

The CPSI T1405N genotype affects the postoperative pulmonary outcomes, such as severe pulmonary hypertension, length of mechanical ventilation and length of ICU stay. Thus, supplementing circulatory citrulline levels according to the methods described herein may be expected to improve the postoperative pulmonary outcomes for a patients with CPSI T1405N genotype undergoing cardiac surgery by maintaining the postoperative pulmonary vascular tone.

Pulmonary Vascular Tone

Increased postoperative pulmonary vascular tone (PVT) is an increase in the contraction of smooth muscle in vessel walls. Increased PVT is a common complication after repair of a variety of congenital heart defects. Steinhorn, et al. *Artificial Organs* (1999) 23: 970-974; Schulze-Neick, et al. *J Thorac Cardiovasc Surg* (2001) 121: 1033-1039. The pathophysiology of increased postoperative PVT is believed to be involved in pulmonary vascular endothelial cell dysfunction. Steinhorn, et al. *Artificial Organs* (1999) 23: 970-974. Limited studies have been performed on the effects that cardiopulmonary bypass (CPB) has on pulmonary endothelial function. In a study of 10 infants undergoing CPB for repair of congenital defects, supplementation of the NO precursor, arginine, ameliorated pulmonary endothelial dysfunction. Schulze-Neick, et al. *Circulation* (1999) 100: 749-755. In animal studies, endothelial cell production of NO is diminished after cardiopulmonary bypass but still a major controlling factor with respect to pulmonary vasomotor tone. Kirshbom, et al. *J thorac Cardiovasc Surg* (1996) 111: 1248-1256.

Increased pulmonary vascular tone (e.g., excessive contraction) is associated with poor outcomes following specific cardiac surgical procedures for congenital heart defects. Steinhorn, et al. *Artificial Organs* (1999) 23: 970-974; Russell, et al. *Anesthesia and Analgesia* 1998; 87:46-51; Yagahi, et al. *Artificial Organs* 1998; 22:886-891; Zobel, et al. *J. of Cardiovascular Surgery* 1998; 39:79-86; Bandla, et al. *Chest* 1999; 116: 740-747; Gamillscheg, et al. *J. of Cardiovascular Surgery* 1997; 113:435-442; Petrossian, et al. *J. of Cardiovascular Surgery* 1999; 117:688-695; Amodeo, et al. *J. of Cardiovascular Surgery* 1997; 114: 1020-1031; Gentles, et al. *J. of Cardiovascular Surgery* 1997; 114:376-391; Freeman, et al. *Pediatr Cardiol* 1995; 16:297-300; Luciani, et al. *Ann Thorac Surg* 1996; 61:800-805; Nakajima, et al. *Pediatr Cardiol* 1996; 17:104-107; Swoonswang, et al. *J Am Coll Cardiol* 1998; 32:753-757; Weinstein, et al. *Circulation* 1999; 100S: II-167-11-170; Ishino, et al. *J. of Cardiovascular Surgery* 1999; 117:920-930; Adatia, et al. *J. of Cardiovascular Surgery* 1996; 112:1403-1405; Mosca, et al. *J. of Cardiovascular Surgery* 2000; 119:1110-1118. To some extent, the type of cardiac defect determines the risk for increased pulmonary vascular tone.

AVSD and VSD Repair:

The highest risk patients for postoperative pulmonary hypertension have cardiac defects associated with excess pulmonary blood flow, such as an atrioventricular septal defect (AVSD) or large unrestrictive ventricular septal defect (VSD). Sustained pulmonary overcirculation can cause hypertrophy and hyperreactivity of pulmonary vascular smooth muscle. Preoperatively, these patients often have congestive heart failure and poor weight gain. Surgical repair is scheduled as early as possible for neonates in order to reduce this postoperative complication.

Bidirectional Glenn and Modified Fontan Procedures:

Patients with single ventricle lesions require surgical procedures where success depends on maintenance of low postoperative pulmonary vascular tone. Staged correction of a single ventricle lesion requires a series of three surgical procedures aimed at separating the pulmonary and systemic circulations. The first of these procedures, often performed in the neonatal period, is a Blalock-Taussig shunt for those patients with a hypoplastic right ventricle or a Norwood I procedure for those patients with hypoplastic left heart syndrome. The second surgery is a bidirectional Glenn shunt where superior vena cava (SVC) flow is diverted directly into the pulmonary artery. The third and final stage is a modified Fontan procedure where inferior vena cava (IVC) flow is diverted into the pulmonary artery, thereby completing separation of the pulmonary and systemic circulations. With the Glenn and Fontan procedures, pulmonary blood flow is entirely passive and relies on an adequate pressure gradient between the venous system (SVC and IVC pressure) and the pulmonary artery (PA) pressure. Any elevation in the pulmonary vascular tone in the immediate postoperative period can lead to decreased pulmonary blood flow and a subsequent fall in cardiac output. On a longer term, elevated pulmonary vascular tone after these procedures can lead to persistent pleural effusions, prolonged requirement for pleural or mediastinal drainage tubes, prolonged ventilation, and prolonged ICU stays. Petrossian, et al. *J. of Cardiovascular Surgery* 1999; 117:688-695; Amodeo, et al. *J. of Cardiovascular Surgery* 1997; 114:1020-1031; Gentles, et al. *J. of Cardiovascular Surgery* 1997; 114:376-391.

Arterial Switch Procedure:

Transposition of the great arteries (TGA) is a complex cardiac lesion that requires surgical correction in the immediate neonatal period. Timing of the arterial switch procedure for correction of TGA specifically takes into account pulmonary vascular tone issues. Freeman, et al. *Pediatr Cardiol* 1995; 16:297-300; Luciani, et al. *Ann Thorac Surg* 1996; 61:800-805; Nakajima, et al. *Pediatr Cardiol* 1996; 17:104-107; Swoonswang, et al. *J Am Coll Cardiol* 1998; 32:753-757. Frequently, surgery is not performed until 5-7 days of age, when perinatal pulmonary vascular tone has partially decreased. Because the right ventricle is the systemic ventricle before surgical correction, postoperative elevations in pulmonary vascular resistance are usually well tolerated and pulmonary artery pressure is usually not measured. However, if postoperative pulmonary vascular tone is increased, it may partially explain why some infants with favorable anatomy and short bypass times still have a complicated postoperative course.

Pulmonary vascular tone can be an important perioperative issue, even for patients not at risk for pulmonary artery hypertension. Protocols for maintaining postoperative pulmonary vascular tone (i.e., reducing or eliminating any increase in PVT) may be helpful in decreasing the need for prolonged mechanical ventilation, ICU stay, and hospitalization. Thus, there exists a need in the art for a more efficient system for maintaining pulmonary vascular tone in a patient during surgery and postoperatively.

SUMMARY OF VARIOUS EMBODIMENTS OF THE INVENTION

The present invention provides a method for maintaining pulmonary vascular tone in a patient undergoing surgery for a cardiac defect, where the method comprises three steps of (a) administering citrulline to the patient at the initiation of the surgery; (b) administering citrulline to the patient during the surgery; and (c) infusing citrulline into the patient after the surgery. This method is particularly beneficial when the cardiac defect is associated with excess pulmonary blood flow and/or when the surgery requires cardiopulmonary bypass. This method may be used when the cardiac defect is an atrial septal defect, particularly when the atrial septal defect is a large arterial septal defect. This method may be used when the cardiac defect is a ventricular septal defect, particularly when the ventricular septal defect is a large unrestrictive ventricular septal defect. This method may be used when the cardiac defect is a single ventricle lesion, such as a single ventricle lesion repaired by Glenn and Fontan procedures. This method may be used when the surgery is an arterial switch procedure.

In many embodiments of the method of this invention, the bolus of citrulline at the initiation of the surgery is about 100-300 mg/kg of citrulline, preferably about 150 mg/kg of citrulline. In many embodiments of the method of this invention, the citrulline administered during the surgery is added to the filtration; in some preferred embodiments, the citrulline administered during the surgery is added to hemoconcentration replacement fluid. The citrulline added during surgery may be added at about 100-300 µmol/L, preferably the citrulline is added at about 200 µmol/L. In many embodiments of the method of this invention, a citrulline bolus is also administered about 15-45 minutes after the surgery, preferably about 30 minutes after the surgery. In particular embodiments of the method of this invention, a citrulline bolus may be administered about 30 minutes after Cardio Pulmonary bypass (CPB) decannulation. In any of these embodiments, the post-surgery citrulline bolus may be about 20 mg citrulline/kg. When infusing citrulline into the patient after surgery according to various embodiments of this invention, citrulline may be infused into the patient for about 48 hours. In many embodiments, the infusion is about 9 mg/kg/hour.

The method of this invention provides for citrulline to be administered perioperatively, and typically the citrulline is administered intravenously. In most embodiments of this invention, the surgical patient's plasma citrulline level is maintained above 30 µmol/L. Preferably, the patient's plasma citrulline level is raised above about 37 µmol/L; more preferably, the patient's plasma citrulline level is raised above about 100 µmol/L. In particular embodiments, the patient's plasma citrulline level is raised above about 100 µmol/L postoperatively; preferably, the patient's plasma citrulline level is raised to about 100-200 µmol/L postoperatively, and the patient's plasma citrulline level may be raised for up to 48 hours postoperatively.

The surgical patients treated according to the method of this invention may be less than about 6 years old; they may even be less than about 10 days old. In particular embodiments, the patient treated according to this invention is at risk for persistent pulmonary hypertension of the newborn (PPHN).

In a particular embodiment, this invention provides a method for maintaining pulmonary vascular tone in a patient undergoing surgery for a cardiac defect comprising: (a) administering about 150 mg/kg of citrulline to the patient at the initiation of the surgery; (b) administering citrulline to the patient at 200 µmol/L to the filtration and hemoconcentration fluid utilized during the surgery; and (c) infusing 9 mg/kg/hour of citrulline into the patient after the surgery for about 4-48 hours. In an alternative embodiment, this invention provides a method for maintaining plasma citrulline levels in a patient undergoing surgery for a cardiac defect comprising: (a) administering about 150 mg/kg of citrulline to the patient at the initiation of the surgery; (b) administering citrulline to the patient at about 200 µmol/L to the filtration and hemoconcentration fluid utilized during the surgery; and (c) infusing about 9 mg/kg/hour of citrulline into the patient after the surgery for about 4-48 hours.

DETAILED DESCRIPTION OF PREFERRED EMBODIMENTS

Figure 1:
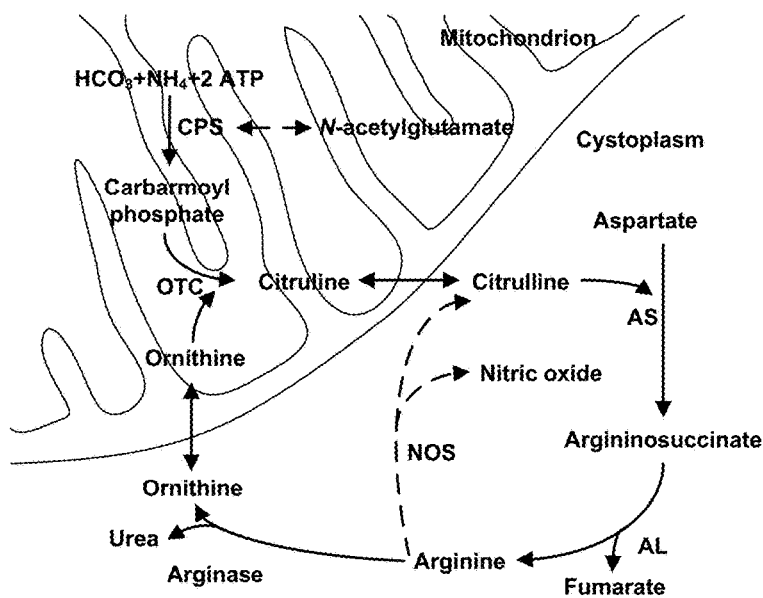
FIG. 1 depicts the hepatic urea cycle.
Figure 2:
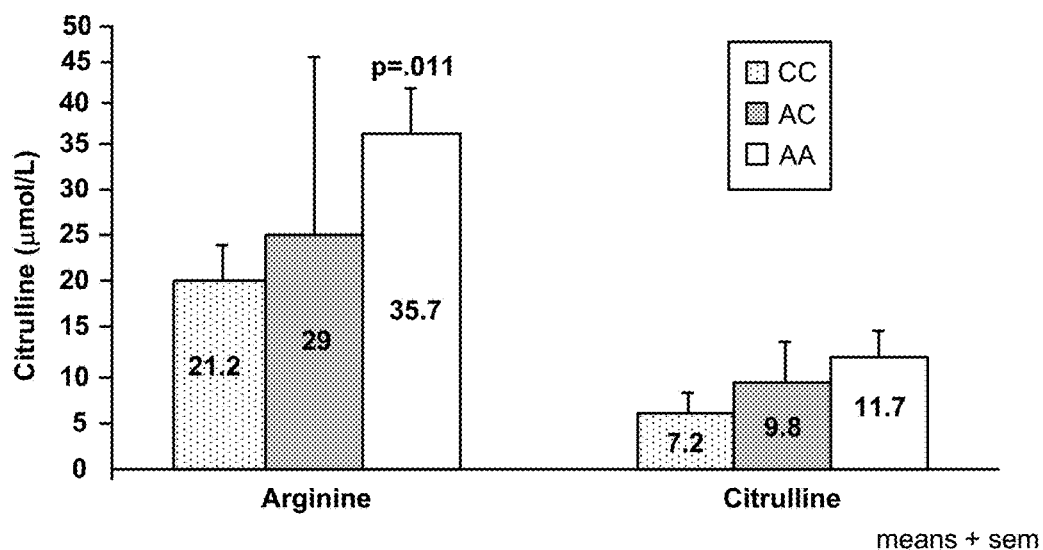
FIG. 2 depicts the effect of genotype of CPSI polymorphisms (CC, AC, and AA) on plasma arginine and citrulline levels. These are CPSI polymorphisms that result in the T1405N genotype.

The invention provides for a method for maintaining pulmonary vascular tone (e.g., avoiding excessive PVT) during surgery and postoperatively by maintaining plasma citrulline levels. A sustained perioperative plasma citrulline level >100 µmol/L for up to 48 hours postoperatively may be achieved by the methods described herein. The inventors surprisingly discovered that intravenous perioperative citrulline supplementation increases postoperative plasma arginine and nitric oxide (NO) metabolite levels and prevents increased postoperative pulmonary vascular tone, leading to a decrease in the duration of postoperative invasive mechanical ventilation. Further, the inventors surprisingly found that a sustained perioperative plasma citrulline level of at least 100 µmol/L for up to 48 hours postoperatively reduces or prevents postoperative elevations in pulmonary vascular tone and shortens the duration of postoperative mechanical ventilation. Improving the postoperative pulmonary tone of the patient reduces costs and frees personnel and equipment for other uses.

The methods described herein may use intravenous L-citrulline for prevention of the clinical sequelae of acute lung injury induced by cardiopulmonary bypass (CPB) in pediatric patients undergoing surgery for congenital heart defects. Cardiopulmonary bypass causes a systemic inflammatory response characterized clinically by acute compromise of cardiovascular and pulmonary function. Apostolakis et al. (2010) *Journal of Cardiac Sugery* 25(1): 47-55; Huffmyer & Groves (2015) "Pulmonary Complications of Cardiopulmonary Bypass." *Best Practice & Research Clinical Anesthesiology*. However, for a number of medical and physiological reasons, pediatric patients subjected to CPB during surgical repair of congenital heart defects are more susceptible to this cascade and at greater medical risk therefrom than adult patients. Kozik & Tweddell (2006) *The Annals of Thoracic Surgery* 81(6): S2347-S2354; Shekerdemian (2009) *Heart* 95(15): 1286-1296; Schure (2010) *Southern African Journal of Anesthesia and Analgesia* 16(1): 46-51. Reduction of key manifestations of acute CPB-induced lung injury, namely the post-operative need for mechanical ventilation and for inotrope therapy may be used to measure clinical effectiveness.

Cardiopulmonary Bypass-induced Injury

A number of factors place the lung at risk for injury during CPB. Chief among these is surface activation of neutrophils and other leukocytes, complement, and cytokines (pro- and anti-inflammatory) inter alia, and an associated systemic inflammatory cascade. Apostolakis et al. (2010) *Journal of Cardiac Sugery* 25(1): 47-55; Schure (2010) *Southern African Journal of Anesthesia and Analgesia* 16(1): 46-51. The degree to which the lung is damaged by the inflammatory response mediated by contact activation of leukocytes during extracorporeal circulation can vary in severity from microscopic changes of no clinical consequence to a capillary leak syndrome, or, in the worst case, to acute respiratory failure.

Pulmonary injury manifests in several ways and may involve both parenchymal and vascular lung tissues. Parenchymal effects of CPB are reflected in alterations in pulmonary compliance, most commonly related to an increase in lung water. The impact of this on the patient is a requirement for increased ventilatory support and a diminished ability of the lungs to perform their function in gas exchange. Vascular effects are manifested by changes in pulmonary vascular resistance, which in turn affect the function of the right ventricle. This condition constitutes in effect, pulmonary arterial hypertension. The lungs are in a unique position in the circulation and may thus be vulnerable to different mechanisms of injury. Circulating leukocytes that elaborate inflammatory mediators following contact with surfaces in CPB apparatus or by direct damage by CPB equipment account for only part of the inflammatory damage that may occur in the lung. Clark (2006) *Perfusion* 21(4): 225-228. The lung is also an important source of inflammatory cells as well as being a target for damage by those same cells. The consequences of the mechanical and inflammatory effects on the lung is decreased functional residual capacity, diminished compliance, and impaired gas exchange. These changes are ultimately associated with increased pulmonary vascular resistance and pulmonary artery pressure.

Inflammation and mechanical factors are not the only factors causing impaired pulmonary function related to cardiopulmonary bypass (CPB). When patients are placed on bypass, the lungs undergo a sudden and significant decrease in perfusion via the pulmonary artery. During total bypass, the lungs receive only nutrient flow from the bronchial arterial circulation. This ischemic effect of CPB is added to its inflammatory effect to produce clinical pulmonary dysfunction. It seems that low-flow CPB produces worse pulmonary injury than does circulatory arrest, which suggests that the interaction between the inflammatory and ischemic components is complex. Both the inflammatory and ischemic factors damage the pulmonary endothelium.

Acute CPB-induced lung injury leads to significant cardiopulmonary problems. The inflammatory response leads to constriction of the pulmonary and systemic vasculature. The constriction leads to increased right ventricular and left ventricular workload. The inflammatory response also leads to pulmonary edema and deterioration in lung compliance and postoperative lung function. The standard treatments for these postoperative complications include mechanical ventilation until the lung function returns to normal and inotropic support until pulmonary and systemic vascular tone returns to normal, eventually decreasing the right and left ventricular workload. Mechanical ventilation and inotropic support are therapies that can thus serve as effective biomarkers of acute CPB-induced lung injury. Additionally, prolonged mechanical ventilation can in turn often lead to other morbidities including ventilator associated lung injury, ventilator associated pneumonia (VAP), central line associated blood stream infections (CLABSI), and even more prolonged intensive care unit stays. Prevention of acute CPB-associated lung injury and its sequelae is therefore a desirable therapeutic goal.

Pediatric CHD Patients

Children undergoing surgery for congenital heart defects are especially susceptible to developing CPB-induced acute lung injury due to age dependent differences in the inflammatory response, and the elevated sensitivity of their immature organ systems to injury as well as distinct differences between paediatric and adult CPB. Kozik & Tweddell (2006) *The Annals of Thoracic Surgery* 81(6): S2347-S2354. Neonates and infants are especially affected as the relatively large extracorporeal circuit size, the blood prime and the need for increased flow rates result in greater exposure of blood to the foreign surface. Schure (2010) *Southern African Journal of Anesthesia and Analgesia* 16(1): 46-51.

For congenital cardiac surgery, the extracorporeal circuit must be adjusted to a wide range of age groups and size variations, from 1.5 kg premature infants to >100 kg adolescents or adults. Infants and children have smaller circulating blood volumes, higher oxygen consumption rates and, often, highly reactive pulmonary vascular beds. In addition, neonates and infants have labile thermoregulation and immature organ systems with multiple implications for ischaemic tolerance and inflammatory response. Many complex repairs require a bloodless operative field, which can be difficult to achieve in the presence of intra or extra cardiac shunts, aortopulmonary collaterals, or otherwise increased pulmonary venous return. Schure (2010) *Southern African Journal of Anesthesia and Analgesia* 16(1): 46-51

The differences between adult and pediatric CPB are shown in

TABLE 1

Tabular overview of differences between adult and paediatric CPB (Schure 2010)

| Parameter | Adult Patient | Paediatric patient |
|---|---|---|
| Estimated blood volume | 65 ml/kg (4-5 litres for 70 kg) | <10 kg: 85 ml/kg (285 ml for 3 kg) |
| Dilution effects on blood volume | 25-33% | 100-200% |
| Addition of whole blood or packed red blood cells to prime | Rarely | Usually |
| Oxygen consumption | 2-3 ml/kg/min | 6-8 ml/kg/min |
| Full CPB flow | 50-75 ml/kg/min | 150-200 ml/kg/min for <3 kg |
| Minimum CPB temperature | Rarely < 25-32° C. | Commonly 15-20° C. |
| Use of total circulatory arrest or regional low flow perfusion | Rare | Common |
| Perfusion pressures | 50-80 mmHg | 20-50 mmHg |
| Acid-base management | Mainly Alpha-stat | Alpha-stat and/or pH-stat |
| Measured PaCO2 | 30-45 mmHg | 20-80 mmHg |
| Glucose regulation hypoglycaemia | Rare (major hepatic injury) | Common; reduced stores |
| hyperglycaemia | Common; treated with Insulin | Less common; risk for rebound hypoglycaemia |

With the possible exception of secundum ASD cases, in which recovery is relatively and consistently robust, there is so far no known biomarker or patient characteristic among pediatric CHD patients linked with the probability of clinically significant CPB-induced ALI. It appears to occur in approximately ⅓ of pediatric CHD surgeries. Russell & Zwass (1998) *Anesthesia & Analgesia* 16(1): 25-27.

The functional and structural status of the pulmonary vascular bed plays a pivotal role in the presentation and outcome of children with congenital cardiovascular disease. However, it is in the immediate postoperative period that these pediatric patients are most vulnerable to CPB-induced acute lung injury. CPB-induced acute lung injury represents a complex interplay between the preoperative condition of the patient (importantly age at repair, type of lesion, and presence of a syndrome) and the inevitable disruption in the endocrine and vasoactive peptide milieu that results from cardiac surgery. Important factors leading to enhanced vasoconstriction are cardiopulmonary bypass, hypothermia, and circulatory arrest with some degree of associated ischemia. Residual cardiac lesions and the sequelae of the stress response, hypoxia, metabolic, and respiratory acidosis may all contribute additional imbalances that favor pulmonary vasoconstriction. Many of the manifestations of acute lung injury associated with CPB can be explained wholly or in part by endothelial dysfunction, which provides at once a possible unifying hypothesis as well as a potential therapeutic target. Acute lung injury associated with CPB may also lead to important adverse cardiac sequelae. The inflammatory response after surgery for CHD is commonly associated with abnormal ventricular-vascular interaction, with systemic vasoconstriction and elevated afterload, as well as with myocardial injury with impaired systolic and diastolic function. In a proportion of patients, these haemodynamic manifestations can lead to the serious consequence of low cardiac output. Shekerdemian (2009) *Heart* 95(15): 1286-1296.

The serious pulmonary and cardiac sequelae of acute lung injury are clinically important to outcome. These sequelae are risk factors for prolonged intensive care stay, and death. Lability of pulmonary vascular tone is common in neonates and infants after surgery for CHD. This can be most problematic after biventricular repairs in patients who had preoperative unrestricted pulmonary flow (large septal defects, common arterial trunk) or pulmonary venous hypertension (obstructed anomalous pulmonary venous drainage). Instability of the pulmonary vascular resistance is also common after palliative surgery in patients with a functionally univentricular circulation, including Norwood-type operations, a systemic-to-pulmonary artery shunt, or a pulmonary artery band. While many therapeutic interventions optimise systemic oxygen delivery through their direct influences on the myocardium and systemic vasculature, manipulation of the pulmonary vascular tone can play an important role in optimising the circulation of children undergoing surgery for heart disease. Shekerdemian (2009) *Heart* 95(15): 1286-1296.

Citrulline, with its mechanism of action, is intended as a preventive treatment to reduce the risk of the development of the sequelae of CPB-associated acute lung injury and thus to positively influence the postoperative recovery of pediatric patients undergoing surgery for congenital heart defects.

Mode of Action

Without being bound to a particular theory, the inventor suggest that when a patient is subjected to cardiopulmonary bypass (CPB), a systemic inflammatory response is induced that is characterized clinically by alterations in cardiovascular and pulmonary function. As part of this response, the pulmonary and systemic vasculature constrict leading to increased right ventricular and left ventricular workload. In addition, the inflammatory response leads to pulmonary edema and deterioration in lung compliance and postoperative lung function. The standard treatments for these postoperative complications include mechanical ventilation until lung function returns to normal and inotropic support until pulmonary and systemic vascular tone returns to normal, with a consequent decrease in the right and left ventricular workload.

It has been demonstrated in multiple observational and clinical studies that plasma levels of citrulline and arginine drop precipitously and do not recover for up to 48 hours after cardiopulmonary bypass for congenital cardiac surgery. Due to intracellular transport mechanisms and intracellular processing, citrulline is the ultimate substrate for endogenous production of nitric oxide. Barr et al. (2003) *The Journal of Pediatrics* 142(1): 26-30; Smith et al. (2006) *The Journal of*

*Thoracic and Cardiovascular Surgery* 132(1): 58-65; Barr et al. (2007) *The Journal of Thoracic and Cardiovascular Surgery* 134(2): 319-326.

The pathophysiology of increased postoperative pulmonary vascular tone (PVT), a known complication after repair of a variety of congenital heart defects, is thought to involve pulmonary vascular endothelial cell dysfunction.

Endogenous nitric oxide (NO) also plays a critical role in the regulation of pulmonary vascular tone. As part of work on defective waste nitrogen processing, it has been found that the hepatic urea cycle has a very important role in the production of two precursors of nitric oxide, namely arginine and citrulline.

Citrulline is a naturally occurring amino acid and the first intermediate in the urea cycle (FIG. 1) as well as a precursor to arginine and nitric oxide (NO). After citrulline is transported intracellularly via a selective membrane transporter, it is rapidly converted to arginine by the enzymes argininosuccinate synthetase (ASS) and argininosuccinate lyase (ASL).

Nitric Oxide, a potent vasodilator, is produced by vascular endothelial cells in response to many different stimuli. Nitric oxide diffuses from the vascular endothelial cell to the vascular smooth muscle cell where it activates guanylate cyclase, leading to increased intracellular levels of cyclic GMP (cGMP). Increased cGMP, in turn, leads to relaxation of the vascular smooth muscle cell and increased blood flow. The extremely short half-life of NO allows for very tight vasoregulation. Citrulline is transported from the mitochondria to the cytoplasm. Argininosuccinate synthetase (ASS) is the first of the cytoplasmic urea cycle enzymes and combines citrulline with aspartate to form argininosuccinate. Argininosuccinatelyase (ASL) cleaves fumarate off from argininosuccinate to form arginine.

The first two steps of the hepatic urea cycle, carried out by carbamyl phosphate synthetase I (CPSI) and ornithine transcarbamylase (OTC), are limited to the liver and gut with the remainder of the pathway distributed throughout the body, including the pulmonary vascular endothelium. Summar (1998) *Journal of Inheritied Metabolic Disease* 21(1): 30-39. In fact, the urea cycle enzymes argininosuccinic acid synthetase (ASS) and argininosuccinic acid lyase (ASL) participate in the NO regeneration pathway in endothelial tissues (FIG. 1). The new substrate supply for this NO pathway comes entirely from the production of citrulline as part of normal urea cycle function. Therefore, a theoretical link exists between NO production and urea cycle function. Carbamyl phosphate synthetase I (CPSI) catalyzes the rate-determining first step of the urea cycle.

A study conducted by Barr revealed that cardiopulmonary bypass significantly decreases several urea cycle intermediates and nitric oxide metabolites after repair of unrestrictive VSD and AVSD, which could have significant clinical implications. Barr et al. (2003) *The Journal of Pedatrics* 142(1): 26-30. Patients undergoing these specific cardiac procedures are at risk for elevated postoperative pulmonary vascular resistance caused by excess preoperative pulmonary blood flow. A decrease in the availability of nitric oxide and its precursors could increase the risk for this postoperative complication.

Of note is the finding that citrulline and arginine levels were decreased in the postoperative period. Citrulline is the first intermediate in the urea cycle after the rate-limiting enzyme carbamyl phosphate synthetase I. Citrulline also crosses mitochondrial and cellular membranes easily and therefore can be transported to other organs in the body. In the pulmonary vascular endothelium, citrulline can then be converted into arginine and subsequently into nitric oxide. Because the majority of circulating arginine is from urea cycle synthesis and not dietary sources, citrulline availability is critical to maintaining adequate arginine supply for nitric oxide production.

Arginine is the substrate for nitric oxide production by nitric oxide synthetase. It was further found that arginine was not decreased immediately after surgery but was significantly decreased at 12, 24, and 48 hours after surgery. The slight lag in the drop in arginine levels compared with citrulline levels may reflect continued synthesis of arginine from precursors available before surgery.

Citrulline and arginine levels continued to decline at 48 hours after surgery. Many of these patients had clinically recovered from their surgery and were ready for transfer out of the PCCU at 48 hours. Depressed citrulline and arginine levels beyond this time point may indicate that these patients are still at risk for increased pulmonary vascular resistance, especially if they are physiologically stressed with hypoxia.

Finally, levels of nitric oxide metabolites decreased throughout the postoperative period. The pathophysiology of decreased production of nitric oxide in congenital heart defects is partially due to pulmonary vascular endothelial cell dysfunction. However, limited studies have been performed on the specific effects of cardiopulmonary bypass on pulmonary endothelial function. In a study of 10 infants undergoing cardiopulmonary bypass for repair of congenital defects, supplementation of the nitric oxide precursor L-arginine was shown to partially ameliorate pulmonary endothelial dysfunction. In animal studies, endothelial cell production of nitric oxide after cardiopulmonary bypass is diminished but is still a major contributor to pulmonary vasomotor tone. Barr et al. (2003) *The Journal of Pedatrics* 142(1): 26-30.

Intravenous L-arginine has been shown to reduce both pulmonary and systemic pressures. This global response would not be tolerated in patients after cardiac surgery, who are already prone to low cardiac output states. The maintenance of high plasma arginine concentrations is also problematic because of poor bioavailability and swift metabolism by intestinal and cytosolic arginase. In contrast administration of intravenous (IV) citrulline is more effective in maintaining plasma L-arginine concentrations than administration of arginine in healthy volunteers. Citrulline has no recognized toxicity and is used as replacement therapy for children with urea cycle defects. I.V. citrulline supplementation is therefore a useful method of increasing arginine and nitric oxide synthesis and maintaining plasma arginine, citrulline, and nitric oxide metabolite levels in the postoperative period. Smith et al. (2006) *The Journal of Thoracic and Cardiovascular Surgery* 132(1): 58-65; Barr et al. (2007) *The Journal of Thoracic and Cardiovascular Surgery* 134(2): 319-326.

Posology

Supplementation trials utilized oral citrulline at a dose of 1.9 g/m$^2$ per dose, administered before cardiopulmonary bypass, postoperatively upon admission to the intensive care unit and every 12 hours at hour 12, 24 and 36. Smith 2006. Oral citrulline was well tolerated with no evidence of significant adverse events (such as systemic hypotension). In addition, it was noted that patients who had a 12-hour plasma citrulline level >37 μmol/L (the upper range of normal levels) did not develop increased PVT. Unfortunately, not all patients receiving oral citrulline reached these levels. These findings helped in the design of subsequent studies with intravenous citrulline. Barr et al. (2007) *The Journal of Thoracic and Cardiovascular Surgery* 134(2): 319-326.

In a dose escalation study targeting a sustained plasma level of around 100 µmol/L, it was noted that intravenous citrulline has a fairly short half-life requiring a classic bolus and continuous infusion drug delivery protocol. Subsequent studies confirmed IV citrulline administration resulting in sustained plasma citrulline levels of approximately 100 µmol/L as follows: An intravenous citrulline bolus of 150 mg/kg or placebo at the initiation of cardiopulmonary bypass, the addition of L-citrulline at a concentration of 200 µmol/L to both the bypass circuit priming fluid as well as to the hemofiltration fluid utilized during cardiopulmonary bypass, and then a bolus of citrulline of 20 mg/kg, 30 minutes after decannulation from cardiopulmonary bypass, immediately followed by initiation of a 9 mg/kg/hr continuous infusion for 48 hours.

Citrulline May be Inadvertently Removed by Hemofiltration and Dialysis

In a large prospective observational study of children undergoing congenital cardiac surgery, plasma citrulline and arginine levels were significantly decreased after surgery and did not return to preoperative baseline levels for up to 48 hours.

Increased pulmonary vascular tone can be an important perioperative issue in children undergoing congenital cardiac surgery, even for patients not thought preoperatively to be at significant risk for severe pulmonary artery hypertension. Clinical safety and pharmacokinetic studies were conducted that show both oral and intravenous citrulline to be well tolerated and without adverse side effects in infants and children undergoing repair of congenital heart defects. A subsequent small randomized placebo controlled trial of citrulline revealed that citrulline was well tolerated with no adverse events; however, in some patients significant citrulline removal occurred during hemofiltration and dialysis performed during cardiopulmonary bypass. In previous studies of potential genetic risk factors for increased PVT, it was noted that the genotype of an important polymorphism in the key urea cycle enzyme carbamyl phosphate synthetase 1 (CPSI T1405N) affects the risk of elevated pulmonary vascular tone in infants and children undergoing surgical repair of congenital heart defects and in neonates at risk for postoperative pulmonary hypertension (PPHN). In addition it was noted that all patients, regardless of polymorphism genotype had a significant decline in plasma levels of key urea cycle intermediates including citrulline and arginine. These associations prompted the inventors to investigate perioperative supplementation with citrulline.

Initial supplementation trials utilized oral citrulline at a dose of 1.9 g/kg before cardiopulmonary bypass, immediately postoperatively and every 12 hours, continuing for 48 hours after surgery. Oral citrulline was well tolerated with no evidence of significant adverse events (such as systemic hypotension). In addition it was noted that patients who had a 12 hour plasma citrulline level >37 umol/L (the upper range of normal levels) did not develop increased PVT.

Unfortunately not all patients receiving oral citrulline reached these levels. These findings helped in the design of subsequent studies with intravenous citrulline. In a dose escalation study targeting a sustained plasma level of around 100 µmol/L, the inventors noted that intravenous citrulline has a fairly short half-life. To address this problem, the inventors developed a combination bolus and continuous infusion drug delivery protocol. The combined protocol of a bolus of 150 mg/kg at the beginning of surgery, followed postoperatively 4 hours later with a continuous infusion of 9 mg/kg/hr, resulted in an sustained plasma citrulline levels of approximately 100 µmol/L. No adverse side effects were noted.

At Vanderbilt, 77 patients have been treated with this protocol. The study was stopped in preparation for a larger multicenter randomized placebo controlled trial. The analysis of the data from these 77 patients revealed that a majority who received citrulline did not reach the therapeutic sustained target plasma citrulline level of about 100 µmol/L, primarily due to a previously unknown removal of citrulline by filtration and hemoconcentration occurring during cardiopulmonary bypass.

Citrulline and Cardiopulmonary Bypass

Intravenous perioperative citrulline supplementation increases postoperative plasma arginine and nitric oxide (NO) metabolite levels and avoids increased postoperative pulmonary vascular tone, leading to a decrease in the duration of postoperative invasive mechanical ventilation. The inventors developed an improved protocol for maintaining pulmonary vascular tone during and after surgery which comprises administration of an intravenous citrulline bolus of 150 mg/kg at the initiation of cardiopulmonary bypass (CPB), the addition of L-citrulline at a concentration of 200 µmol/L to the filtration or hemoconcentration replacement fluid utilized during cardiopulmonary bypass, a citrulline bolus of 20 mg/kg 30 minutes after CPB decannulation, immediately followed by the start of a 9 mg/kg/hr continuous infusion for 48 hours.

This revised protocol is designed to maintain a sustained therapeutic plasma citrulline level above the target threshold of about 100-200 µmol/L from the initiation of cardiopulmonary bypass, throughout surgery, and for up to about 48 hours after surgery.

Separate IV access is not required for citrulline. The citrulline formulation is isotonic and can run through either a peripheral IV or a central venous catheter. Citrulline is an amino acid and thus for compatibility purposes may be treated like parental nutrition. Additionally, citrulline is compatible with fluids used for filtration or hemoconcentration during cardiopulmonary bypass.

Figure 3:
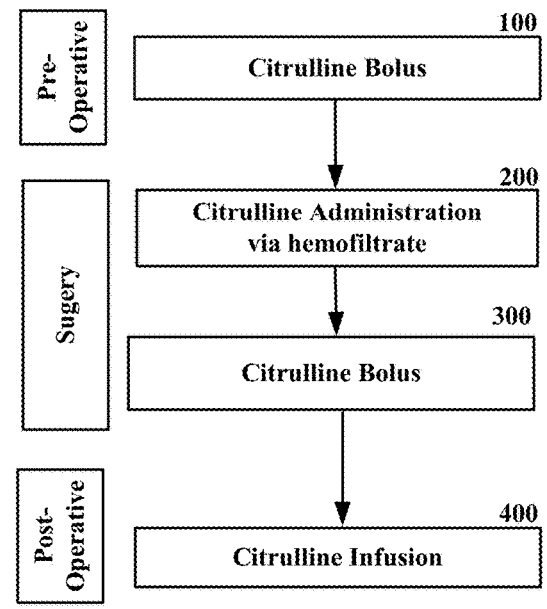
FIG. 3 depicts a flow-chart of an exemplary protocol to maintain postoperative pulmonary vascular tone in cardiac surgery.

Referring to FIG. 3, an exemplary flow chart shows a method of maintaining pulmonary vascular tone comprising administering citrulline to a patient during surgery.

With reference to FIG. 3, during pre-operative stage, a citrulline bolus of 150 mg/kg may be administered to the patient 100. During surgery, citrulline may be administered at a concentration of 200 µmol/L to the filtration or hemoconcentration replacement fluid utilized during surgery 200. During post-operative stage, a citrulline bolus of 20 mg/kg may be administered 300 and may be followed by a 9 mg/kg/hr continuous infusion for 48 hours 400.

Citrulline Formulations

Citrulline (2-amino-5-(carbamoylamino)pentanoic acid) [$C_6H_{13}N_3O_3$] is an amino acid. Citrulline solution for IV administration may be manufactured by methods known in the art. See, e.g., Kakimoto, et al. (1971) *Appl Microbiol* 22(6): 992-999.

Methods of Use

The citrulline may be administered during a surgical procedure. The suitable dosing may include an intravenous citrulline bolus of 150 mg/kg at the initiation of cardiopulmonary bypass, the addition of L-citrulline at a concentration of 200 µmol/L to the filtration and hemoconcentration fluid utilized during cardiopulmonary bypass, and a bolus of 20 mg/kg of citrulline 30 minutes after decannulation from cardiopulmonary bypass, immediately followed by a 9 mg/kg/hr continuous infusion for 48 hours. The filtration or hemoconcentration replacement fluid may be provided as standard fluid (e.g., Plasmalyte) with citrulline added to achieve a citrulline concentration of 200 µmol/L. Doses may be given by a central intravenous catheter that will be placed after induction of anesthesia or via the bypass circuit.

Citrulline may be infused into a patient by an intravenous route to maintain a plasma citrulline level. A protocol for maintaining pulmonary vascular tone during surgery may comprise administration of an intravenous citrulline bolus (e.g., of 150 mg/kg) at the initiation of cardiopulmonary bypass (CPB), the addition of citrulline (e.g., at a concentration of 200 µmol/L) to the filtration or hemoconcentration replacement fluid utilized during surgery, optionally cardiopulmonary bypass, a citrulline bolus (e.g., 20 mg/kg) 30 minutes after CPB decannulation, immediately followed by the start of a continuous infusion (e.g., 9 mg/kg/hr) for 48 hours.

The intravenous citrulline bolus at the initiation of cardiopulmonary bypass (CPB) may be about 100-300 mg/kg. The intravenous citrulline bolus at the initiation of cardiopulmonary bypass (CPB) may be about 100, 125, 150, 175, 200, 225, 250, 275, or 300 mg/kg. In a preferred mode, the intravenous citrulline bolus at the initiation of cardiopulmonary bypass (CPB) may be about 150 mg/kg.

Citrulline may be added at a concentration of about 100-300 µmol/L to the filtration or hemoconcentration replacement fluid utilized during surgery, optionally including cardiopulmonary bypass. Citrulline may be added at a concentration of about 100, 125, 150, 175, 200, 225, 250, 275, or 300 µmol/L to the filtration or hemoconcentration replacement fluid utilized during surgery, optionally during cardiopulmonary bypass. In a preferred mode, the citrulline may be added at a concentration of about 200 µmol/L to the filtration or hemoconcentration replacement fluid utilized during surgery, optionally during cardiopulmonary bypass.

The citrulline bolus administered 30 minutes after decannulation, typically after cardiopulmonary bypass, may be about 10-30 mg/kg. A citrulline bolus of about 10, 15, 20, 25, or 30 mg/kg may be administered shortly after the conclusion of cardiopulmonary bypass, typically about 30 minutes after decannulation. In a preferred mode, a citrulline bolus of about 20 mg/kg may be administered typically 30 minutes after decannulation, following cardiopulmonary bypass.

The continuous infusion may be at about 5-15 mg/kg/hour citrulline—about 5, 6, 7, 8, 9, 10, 11, 12, 13, 14, or 15 mg/kg/hour citrulline. In a preferred mode, the continuous infusion may be at about 9 mg/kg/hour citrulline.

Alternatively, citrulline may be administered orally at a dosage of about 5-15 g/kg, i.e., about 5, 6, 7, 8, 9, 10, 11, 12, 13, 14, or 15 g/kg of citrulline. In a preferred mode, the oral dosage of citrulline may be about 9 g/kg of citrulline.

The target level for plasma citrulline may be maintained at about 50-300 µmol/L; For example, the plasma citrulline level may be maintained at about 50, 75, 100, 125, 150, 175, 200, 225, 250, or 300 µmol/L. In a preferred mode, the plasma citrulline level may be maintained at about 100 µmol/L.

The citrulline may be provided in dose unit form. For example, the citrulline may be provided in a container containing 300 mg sterile citrulline formulated for injection. This may be reconstituted for use using 6 mL sterile water and further diluted with approximately 5.9 mL sterile NaCl solution 0.9% Ph. Eur. to a total volume of 12 mL and a concentration of 300 mg/12 mL (i.e., 25 mg/mL). The citrulline may be formulated for injection at a concentration of 10-40 mg/mL, for example 10, 15, 20, 25, 30, 35, or 40 mg/mL. The citrulline may be provided as a drug product at 500 mg sterile citrulline for injection in 10 mL of sterile water. This may be used to infuse patients using sodium chloride 0.9% Ph. Eur.

In one embodiment, on the day of the surgery the patient is administered a bolus of 150 mg/kg citrulline, adding citrulline at 200 µmol/L to the filtration and hemoconcentration fluids. About 30 minutes post-surgery, a bolus of 20 mg/kg citrulline is administered and a continuous intravenous infusion of citrulline at 9 mg/kg/hour is started after the bolus (e.g., within 5-10 minutes, preferably immediately following the administration of the bolus) and maintained for 6-48 hours, preferably for 48 hours.

For example, an L-citrulline bolus of 150 mg/kg can be administered at the initiation of cardiopulmonary bypass (CPB) with citrulline at a concentration of 200 µmol/L added to the filtration and hemoconcentration fluid utilized during CPB; a bolus of 20 mg/kg of L-citrulline can be administered 30 minutes after decannulation from CPB, immediately followed by a 9 mg/kg/hr continuous infusion of L-citrulline for 48 hours. Doses can be administered by a central IV catheter that may be emplaced after induction of anesthesia or via the bypass circuit. Separate IV access is not required for this drug administration. Citrulline is isotonic and can run through either a peripheral IV or a central venous catheter. Citrulline is an amino acid, and thus, for compatibility purposes, the drug product is treated like parenteral nutrition. Additionally, it is compatible with fluids used for filtration or hemoconcentration during CPB.

Postoperative Parameters

The clinical outcome of patients treated with intravenous citrulline may be assessed by: the necessity and length of postoperative mechanical ventilation, incidence of increased postoperative PVT by echocardiograms, serum creatinine and liver enzyme levels, Inotrope score, length and volume of chest tube drainage, length of ICU stay, length of hospitalization, and/or survival rate.

Postoperative Mechanical Ventilation: The duration of postoperative invasive mechanical ventilation is the time in hours from separation from cardiopulmonary bypass until endotracheal extubation. A decrease in the time spent on postoperative invasive mechanical ventilation is a positive postoperative outcome.

Incidence of Increased Postoperative PVT by Echocardiograms: Increased PVT is defined as a right ventricular (RV) pressure >½ systemic arterial pressure. If postoperative PVT remains unchanged, as compared to a control group, this is a positive postoperative outcome.

Serum Creatinine & Liver Enzymes: Serum electrolyte, creatinine, and CBC Levels may be recorded daily from admission to PCCU until PCCU discharge. Additionally, liver enzymes may be obtained during the baseline, 24 hour, and 28 day/discharge periods. If serum electrolyte, creatinine, and CBC Levels are comparable to a control group, this would be a positive postoperative outcome.

Inotrope Score: The inotrope dose should be monitored post operatively from the time of PCCU admission using the following scoring system:

$$\begin{array}{r} \text{Dopamine (mcg/kg/min)} \times 1 \\ \text{plus Dobutamine (mcg/kg/min)} \times 1 \\ \text{plus Milrinone (mcg/kg/min)} \times 10 \\ \text{plus Epinephrine (Adrenaline)(mcg/kg/min)} \times 100 \\ \text{plus Phenylephrine (mcg/kg/min)} \times 100 \\ \underline{\text{plus Norepinephrine (Noradrenaline)(mcg/kg/min)} \times 100} \\ = \text{total inotrope score} \end{array}$$

See, e.g., Hoffman, et al. *Circulation* (2003) 107: 996-1002. A decrease in the inotrope score would be a positive postoperative outcome.

Length and volume of chest tube drainage: The total postoperative length in hours and total volume of chest tube drainage in cc prior to discontinuation of the chest tubes by the surgical team may be recorded. A decrease in the postoperative length of time and/or total volume of chest tube drainage, as compared to a comparison group, would be a positive postoperative outcome.

Length of ICU stay: Length of ICU stay may be calculated in two ways: (1) as total number of postoperative days spent in an ICU or ICU step down bed until the patient has been cleared by the physician team to be ready for transfer to a non-ICU area; and (2) as total number of hours postoperative that the patient required either mechanical ventilator or continuous intravenous inotrope or vasodilator support. A decrease in the length of ICU stay by either of these measures would be a positive postoperative outcome.

Length of hospitalization: Length of hospitalization may be calculated as the total number of days postoperative until discharge from the hospital. A decrease in the length of hospitalization would be a positive postoperative outcome.

Survival: Both 28 day postoperative survival and survival to discharge home from the hospital may be recorded. Increased survival after 28 days postoperative would be a positive postoperative outcome.

The inventors surprisingly discovered that intravenous L-citrulline delivery given peri-operatively reduces the sequelae of acute cardiopulmonary bypass-induced lung injury as evidenced by the reduction of post-operative need for mechanical ventilation and inotrope therapy in pediatric subjects undergoing repair of congenital heart defects.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in surgery, biochemistry, medicine, physiology, and/or related fields are intended to be within the scope of the following claims.

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The examples contained herein are offered by way of illustration and not by any way of limitation.

EXAMPLES

Example 1

Arginine, Citrulline, and Plasma Nitrate Levels and Risk of PPHN

Figure 4:
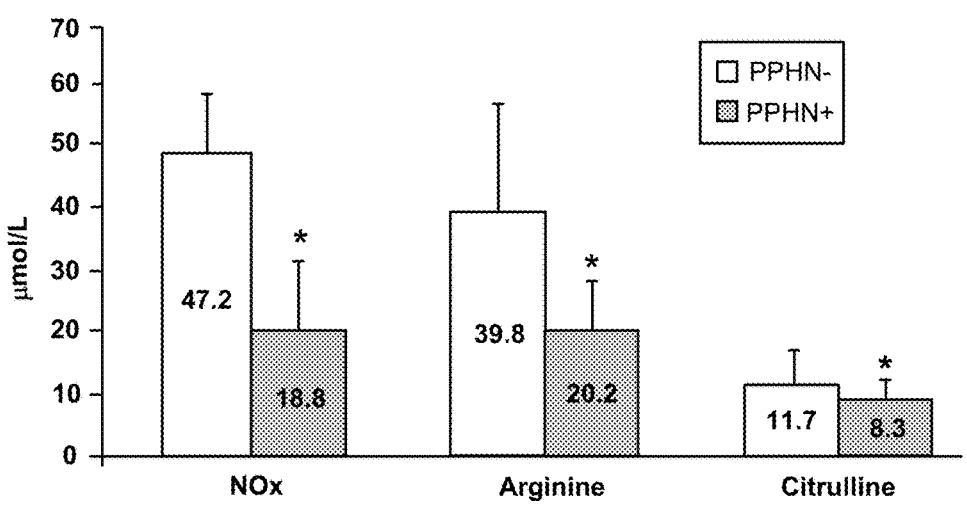
FIG. 4 depicts the reduction of NO and NO precursors, arginine and citrulline, in patients with persistent pulmonary hypertension in the newborn (PPHN).

Neonates who developed PPHN had lower arginine, citrulline, and plasma nitrate levels as compared to infants without PPHN. Ten neonates had plasma NO metabolites (NOx) measured using the modified Griess reaction; 5 were PPHN+ and 5 were PPHN−. The PPHN+ cases had a significantly lower mean level of NOx, (p=0.006) (FIG. 4). The neonates with PPHN had significantly lower plasma arginine and citrulline levels on amino acid analysis (FIG. 4). There were no significant differences in the levels of any other individual amino acids between the two groups. The number of subjects was too small to evaluate relationships between NOx and amino acid levels and genotype. This data shows that infants with PPHN have decreased urea cycle intermediates and products.

Example 2

Urea Cycle Function in Infants and Children Undergoing Cardiopulmonary Bypass for Correction of Congenital Heart Defects The prevalence of increased postoperative pulmonary vascular tone and status of urea cycle function in infants and children undergoing cardiac surgery was studied. Over a 20-month period, 169 infants and children who required one of the 6 specific surgical procedures for correction of their congenital heart defects were prospectively studied. See Table 1. After parental consent, all patients had blood drawn for genotype before surgery and blood collected for amino acid analysis at 5 different time points (pre-op, immediately postoperative, 12 hours, 24 hours and 48 hours postoperative). All patients, except those undergoing a Stage I Norwood, were monitored for increased postoperative pulmonary vascular tone (PVT+) defined as a mean PA pressure >20 mmHg. Infants undergoing a Stage I Norwood were defined as PVT+ if they had a clinical requirement for inhaled NO utilized for arterial saturations <60% with adequate systemic pressures.

Table 1 shows the average age for each of the six procedures and the length of cardiopulmonary bypass exposure. Of 169 patients, 56 (33.1%) developed clinical evidence of increased postoperative pulmonary vascular tone (PVT+). Many of these patients required clinical intervention including sedation, paralysis, and hyperventilation. Thirty-three patients were treated with inhaled NO (NO+).

TABLE 1

Type of Surgical Procedure Performed in Study Population

| Procedure | # | Age (mos) | CPB(min) | PVT+ | NO+ |
|---|---|---|---|---|---|
| Bidir Glenn Shunt | 42 | 6.4 ± 2.5 | 84 ± 36 | 18 (42.9%) | 10 (23.8%) |
| Norwood Stage I | 33 | 0.8 ± 0.8 | 112 ± 32 | 14 (42.4%) | 9 (27.3%) |
| VSD closure | 36 | 8.5 + 11.9 | 91 + 21 | 15 (41.7%) | 1 (2.8%) |
| AVSD repair | 24 | 5.2 + 2.5 | 111 + 27 | 12 (50%) | 3 (12.5%) |
| Arterial Switch | 18 | 0.6 + 1.3 | 157 + 38 | 6 (33.3%) | 2 (11.1%) |
| Modified Fontan | 16 | 24.8 + 18.8 | 94 + 25 | 4 (25%) | 3 (18.8%) |
| Total # of patients | 169 | 6.8 ± 10.6 | 104 ± 37 | 56 (33.1%) | 33 (19.5%) |

Infants and children undergoing cardiac surgery showed an increased postoperative pulmonary vascular tone and status of urea cycle function.

Effect of Cardiopulmonary Bypass on Urea Cycle Function

Figure 5:
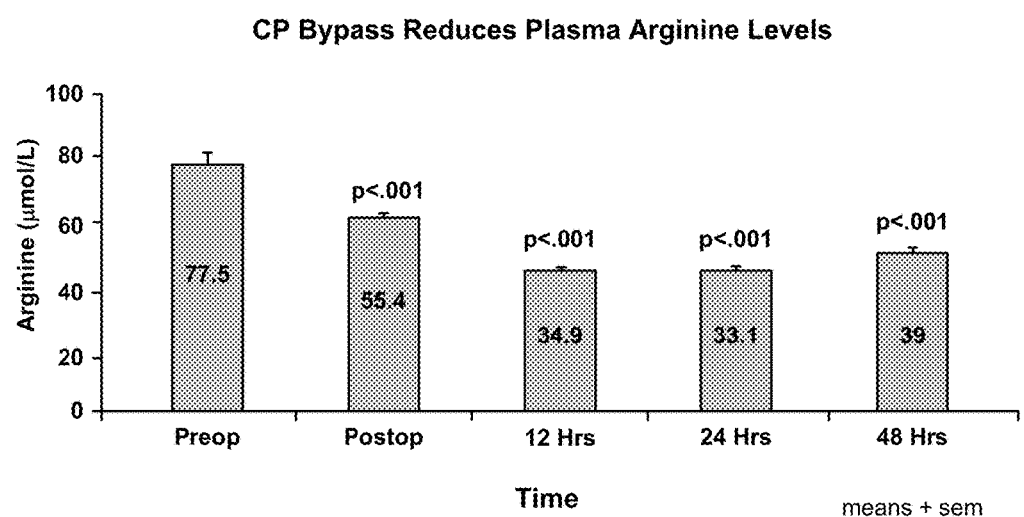
FIG. 5 depicts the reduction of plasma arginine levels from cardiopulmonary bypass (CP bypass).
Figure 6A:
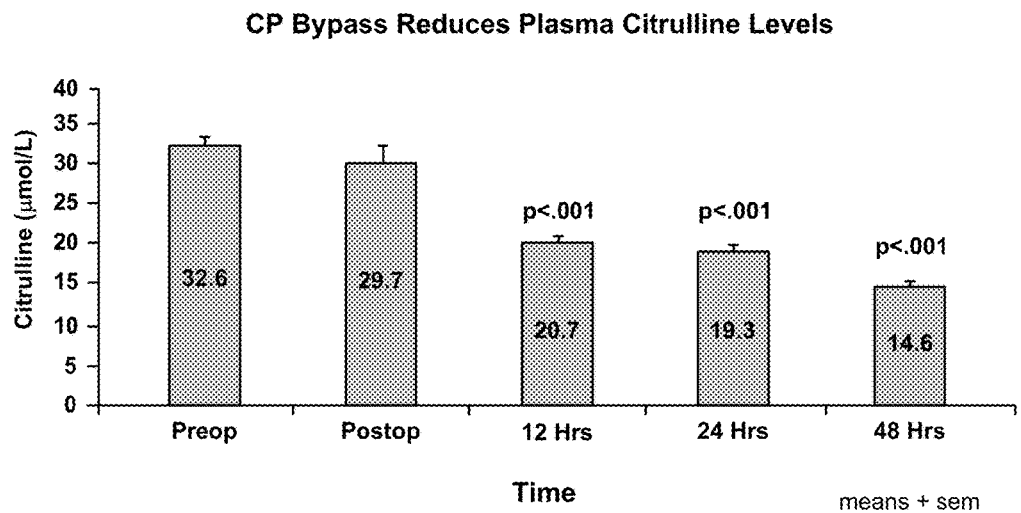
FIG. 6A-B depicts the reduction of plasma and serum citrulline levels from cardiopulmonary bypass.
Figure 6B:
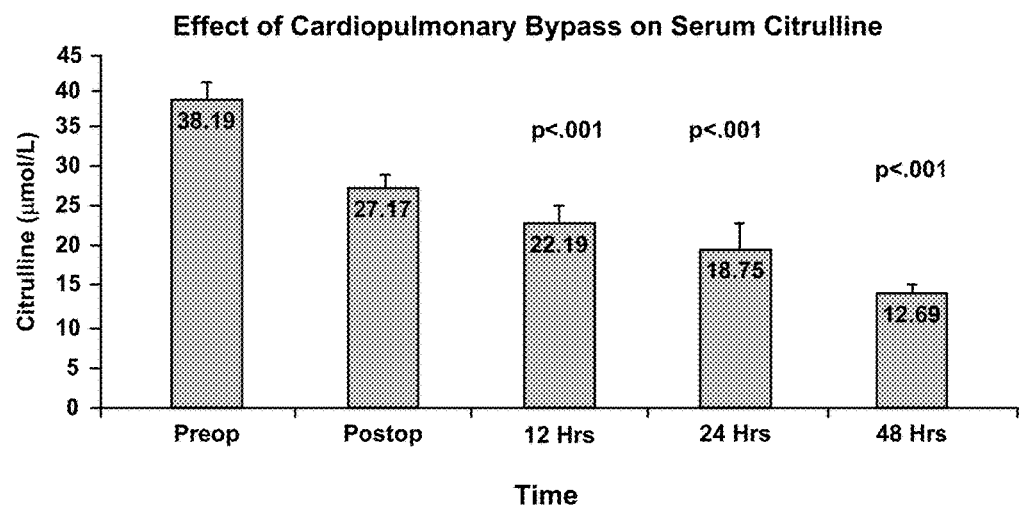
Figure 7:
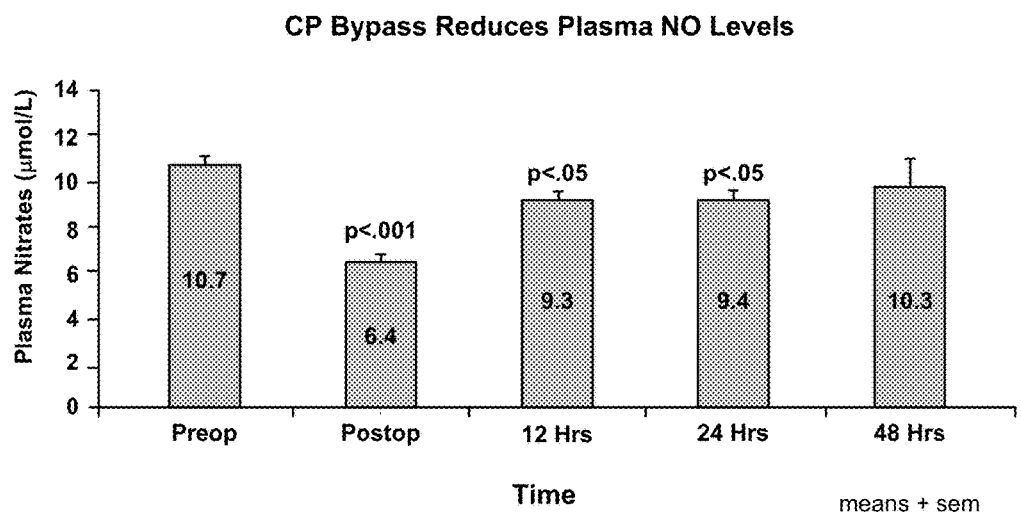
FIG. 7 depicts the reduction of plasma nitric oxide (NO) levels from cardiopulmonary bypass.

To test whether a cardiopulmonary bypass would decrease urea cycle function and NO availability, perioperative urea cycle intermediates and plasma nitric oxide metabolites were analyzed. Plasma samples were collected from each of the 169 patients at 5 perioperative time points and were analyzed by cation exchange chromatography using a Beckmann 7300 amino acid analyzer (Beckmann, Palo Alto, Calif.). Arginine and citrulline were used as the primary markers of urea cycle flux. Plasma nitric oxide metabolite levels were used as an indirect measure of NO availability utilizing a colorimetric assay with modified Griess reagents and read at 540 nm absorbance. All patients required cardiopulmonary bypass for correction of their cardiac defects. Within the study population, cardiopulmonary bypass caused a significant decrease in mean arginine levels at all postoperative time points compared to preoperative levels (FIG. 5). A similar decrease was seen in mean citrulline levels (FIG. 6A-B). Plasma NO metabolite levels were also depressed immediately after surgery but showed a partial rebound at 12 and 24 hours before returning to preoperative levels at 48 hours (FIG. 7). In contrast, there was no effect of bypass on total amino acids not involved in the urea cycle. Because amino acids not involved in the urea cycle were not affected, this data suggests that the effect on urea cycle function and NO substrate synthesis may last for up to about 48 hours after surgery.

Figure 8:
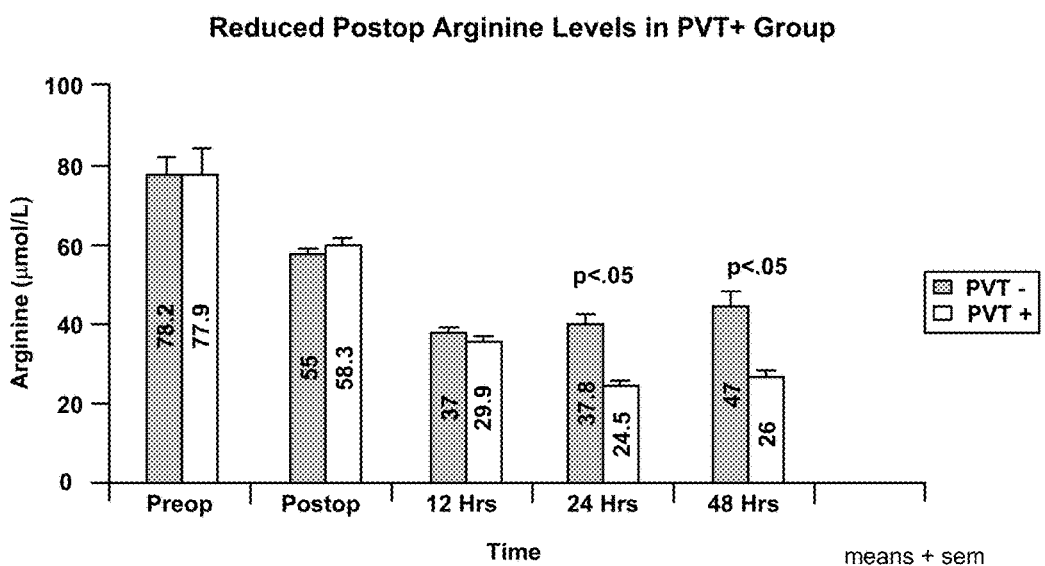
FIG. 8 depicts the reduction of arginine levels in patients with and without increased pulmonary vascular tone (PVT− and PVT+) preoperatively, postoperatively, and 12, 24, and 48 hours postoperatively.

In patients who subsequently developed increased postoperative PVT (PVT+), a decrease in plasma arginine levels was noted compared to patients without increased PVT (PVT−). FIG. 8. Similar observations were not noted for citrulline and NO metabolites.

Using linear regression, the length of cardiopulmonary bypass did not show any affect on plasma citrulline, and arginine, NO metabolite levels at any of the postoperative time points.

Summary of Clinical Results

This study shows cardiopulmonary bypass used for correction of congenital heart defects causes a significant decrease in urea cycle function with a large decrease in availability of precursors for nitric oxide synthesis. Cardiopulmonary bypass used for surgical correction of congenital heart defects caused a fairly significant decrease in availability of nitric oxide precursers in the urea cycle and nitric oxide levels measured indirectly by plasma NO metabolites. Because amino acids not involved in the urea cycle were not affected, an effect on urea cycle function and NO substrate synthesis may last up to 48 hours after surgery. Patients with increased postoperative pulmonary vascular tone had a more significant decrease in arginine levels than those with normal tone.

A separate study showed the risk of increased postoperative pulmonary vascular tone was influenced by CPSI T1405N genotype. Arginine levels were significantly different among CPSI T1405N genotypes at 48 hours after surgery.

Example 3

Intravenous Citrulline Supplementation Increases Plasma Arginine Levels

The objective was to assess the safety of intravenous citrulline and its effect on serum arginine levels in piglets. A total of 9 Duroc swine, aged 5-21 days, with a target minimum weight of 4 kg were utilized. All piglets underwent anesthetic induction and tracheostomy. Central lines were placed in the femoral artery and femoral vein and hemodynamics monitored continuously. Citrulline (600 mg/kg IV) was administered to 5 piglets. Saline was given to control animals. Serum amino acids were drawn before and each hour after citrulline administration.

Serum arginine levels peaked at 1-2 hours following intravenous citrulline administration and remained sustained above baseline three hours following, reaching significance at all time points compared to controls (p<0.001). No hemodynamic instability was observed. See Tables 2-3.

TABLE 2

Arginine Levels (μmol/L) Following intravenous citrulline

| Treatment Group (n = 5) | Baseline | 1 hour post | 2 hours post | 3 hours post |
|---|---|---|---|---|
| L-Citrulline (600 mg/kg) | 131.5 | 535.0 | 559.8 | 498.4 |
| Control (saline) | 89.6 | 103.0 | 118.1 | 136.7 |
| p-value | 0.1582 | <0.001 | <0.001 | <0.001 |

TABLE 3

Mean Arterial Blood Pressures (mmHg) Following intravenous Citrulline

| Treatment Group (n = 4) | Pre-dose | 1 hour post | 2 hours post | 3 hours post |
|---|---|---|---|---|
| L-Citrulline (600 mg/kg) | 67.0 | 67.4 | 64.8 | 62.2 |
| Control (saline) | 53.2 | 58.7 | 55.7 | 54.7 | p > .05 at all time points

Therefore, intravenous administration of citrulline leads to sustained increase in plasma citrulline and arginine levels.

Example 4

Perioperative Oral Citrulline Supplementation in Children Undergoing Congenital Cardiac Surgery The purpose of this study was to assess absorption and demonstrate safety of oral citrulline as a potential alternative to IV citrulline. 40 patients with one of the 5 surgical diagnoses identified above were randomized to receive 5 doses of oral citrulline (1.9 grams/kg) vs. placebo. The first dose was administered immediately prior to surgery and the second dose immediately on arrival in the Pediatric ICU after surgery followed every 12 hours×3 doses. Plasma citrulline levels were significantly higher in the citrulline group (36 vs. 26 μmol/L, p=0.013) demonstrating adequate absorption.

TABLE 4

Serum Levels 12 hours postoperative with and without PHTN

| Serum Citrulline level 12 hours postop | No PHTN | +PHTN |
| --- | --- | --- |
| <37 μmol/L | 18 patients | 9 patients |
| >37 μmol/L | 12 patients | 0 patients | p value = 0.036 (Fisher's exact)

The study was not adequately powered to detect an effect on the incidence of postoperative pulmonary hypertension (PHTN), however, patients with a plasma citrulline level >37 μmol//L did not develop pulmonary hypertension.

Example 5

Administration of Citrulline During Surgery

The initial goal was to test the safety and pharmacokinetics of three doses of intravenous citrulline in children undergoing surgical repair of specific congenital heart defects. Intravenous citrulline administration had a theoretical risk of systemic arterial hypotension. An adverse drop in mean arterial pressure was defined as a greater than a twenty percent decrease from baseline. The baseline postoperative mean arterial blood pressure was calculated as the average of mean arterial blood pressure measurements collected every 5 minutes for the 30 minutes immediately preceding the administration of the postoperative dose or infusion. The bedside monitor was then set to alarm if that 20% drop was reached at any time in the 48 hour study period.

Figure 9A:
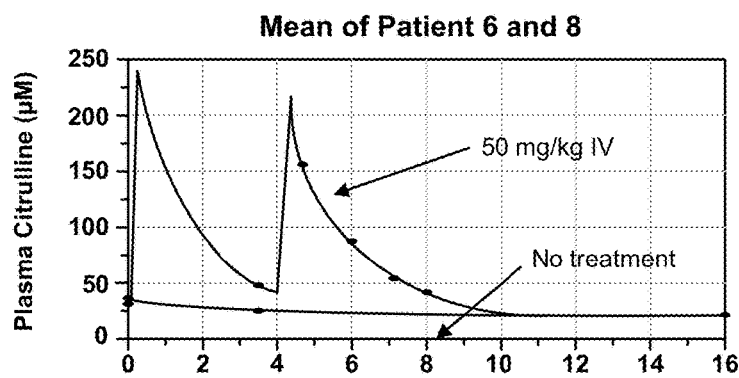
FIG. 9A-C depicts the citrulline plasma levels in patients with and without administration of a bolus of citrulline. The patients received a dose of citrulline (50, 100, or 150 mg/kg) preoperatively and postoperatively.
Figure 9B:
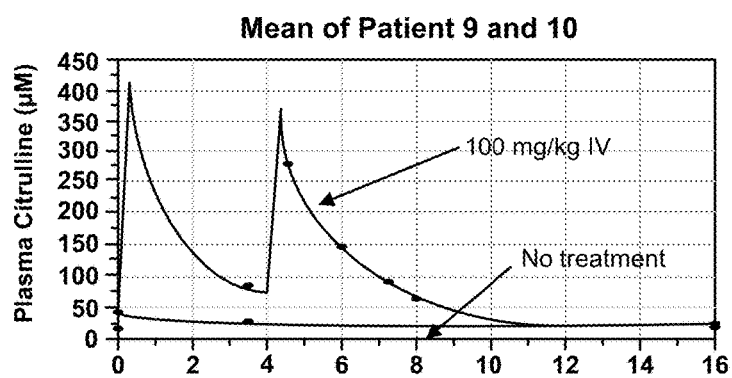
Figure 9C:
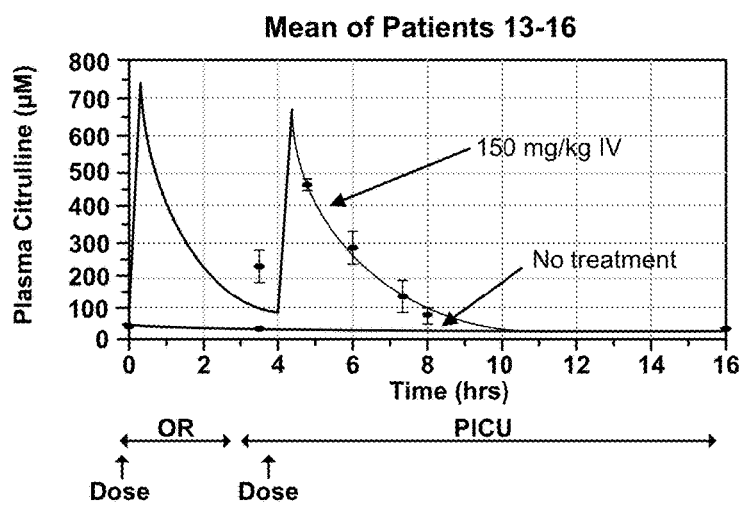

The original doses selected were 200, 400, and 600 mg/kg based on data from previous animal studies. The original study design was a 4 arm study using the 3 doses and a placebo control. Five patients were enrolled and the Data Safety and Monitoring Board (DSMB monitor promptly noted that the plasma levels achieved with these doses were very high although no adverse effects were noted. Subsequently the study design was changed to an open label dose escalation trial starting at 50 mg/kg and escalated the dose in 50 mg/kg intervals. Each patient received 2 doses, 1 dose in the operating room after initiation of cardiopulmonary bypass and one 4 hours later in the intensive care unit. The data is summarized in FIGS. 9A-C.

Figure 10:
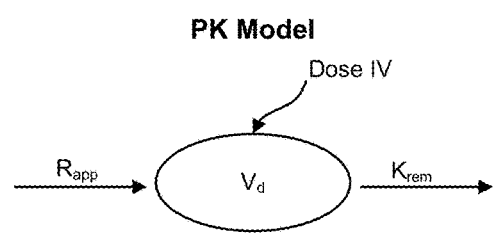
FIG. 10 depicts a PK model and PK parameters.

Patients 6 and 8 received 50 mg/kg of intravenous citrulline and had a peak citrulline level of approximately 220 μmol/L and a 4 hour trough level of 40 μmol/L. No adverse side effects were noted. This trough was well below the target range of 80-100 μmol/L and the dose was subsequently increased. Patients 9 & 10 received 100 mg/kg of intravenous citrulline and had a peak citrulline level of 375 μmol/L and a 4 hour trough of 50 μmol/L. Again, no adverse side effects were noted. This trough was also below the target range of 80-100 μmol/L and the dose was subsequently increased. Patient 13-16 received 150 mg/kg of intravenous citrulline and had a peak citrulline level of 660 μmol/L and a 4 hour trough of 80 μmol/L. This 4 hour trough was in the target range of 80-100 μmol/L and the dose was not escalated further. The pharmacokinetic profile of these 3 doses of citrulline is summarized in FIG. 10.

Figure 11A:
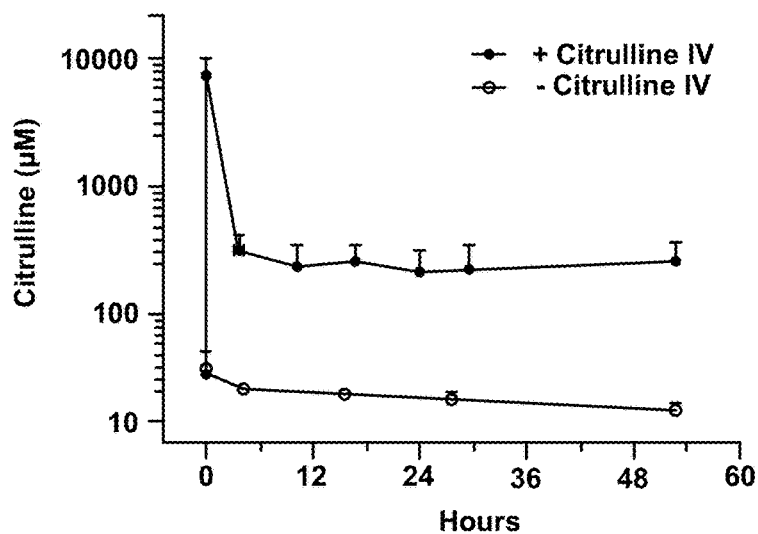
FIG. 11A depicts the mean citrulline levels in infants with and without the administration of intravenous citrulline ("citrulline IV") over 60 hours.
Figure 11B:
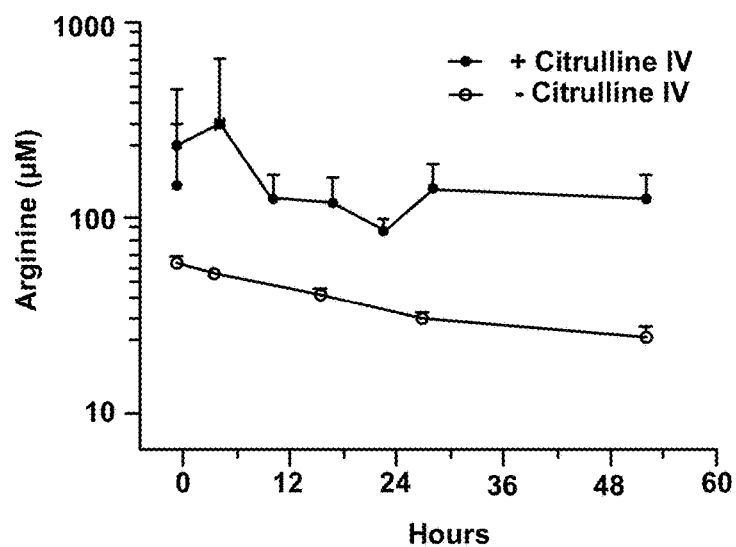
FIG. 11B depicts the mean arginine levels in infants with and without the administration of intravenous citrulline ("citrulline IV") over 60 hours.

The half life was calculated to be approximately 85 minutes which was too short to proceed with intermittent dosing. After pharmacokinetic modeling, the study design was changed to a bolus dose of 150 mg/kg given in the OR on cardiopulmonary bypass followed 4 hours later by a continuous infusion of 9 mg/kg/hour for 48 hours. Another 9 patients were enrolled. The mean plasma levels of both citrulline and arginine in study patients (+IV citrulline) compared to patients in the observational cohort (−IV citrulline) are depicted in FIGS. 11A-B.

There was one significant adverse event but it was not related to the use of IV citrulline. The patient developed a bradycardic arrest approximately 8 hours after an AVSD repair that was not preceded by systemic hypotension. The patient required emergent ECMO support for 48 hours and subsequently fully recovered and was discharged home on hospital day 22. The DSMB reviewed the case and determined that the significant adverse event was unlikely to be related to the citrulline administration.

Based on this data, it was determined that intravenous citrulline was safe and that the combination of a bolus of 150 mg/kg given on cardiopulmonary bypass at the beginning of surgery followed 4 hours later by a continuous infusion of 9 mg/kg/hr may maintain the pulmonary vascular tone postoperatively.

Example 6

Figure 12:
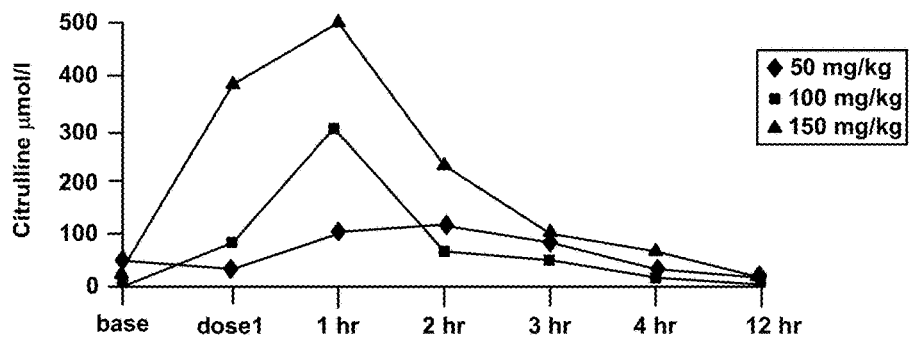
FIG. 12 depicts the plasma citrulline levels in patients administered a dose of citrulline (50, 100, or 150 mg/kg) postoperatively over 12 hours.

Perioperative Intravenous L-Citrulline Pharmacokinetics in Children Undergoing Congenital Cardiac Surgery To determine clearance of a single bolus dose of IV citrulline and optimal dose frequency, a dose escalation design using three concentrations of IV citrulline: 50, 100, & 150 mg/kg was utilized. The dose of citrulline was given in the operating room immediately after cannulation and initiation of cardiopulmonary bypass. The overall goal was to achieve a sustained citrulline level of 100 μmol/L or more up to four hours after the initial dose. The four hour time point was selected to allow for the surgical procedure to be completed and the patient to return to the ICU postoperatively before further dosing. The composite citrulline data is shown in FIG. 12.

From this data it was determined that 150 mg/kg was the optimal dose as it resulted in four hour levels close 100 μmol/L. There were no adverse effects including hypotension from administration of any of the concentrations of IV citrulline.

Figure 13:
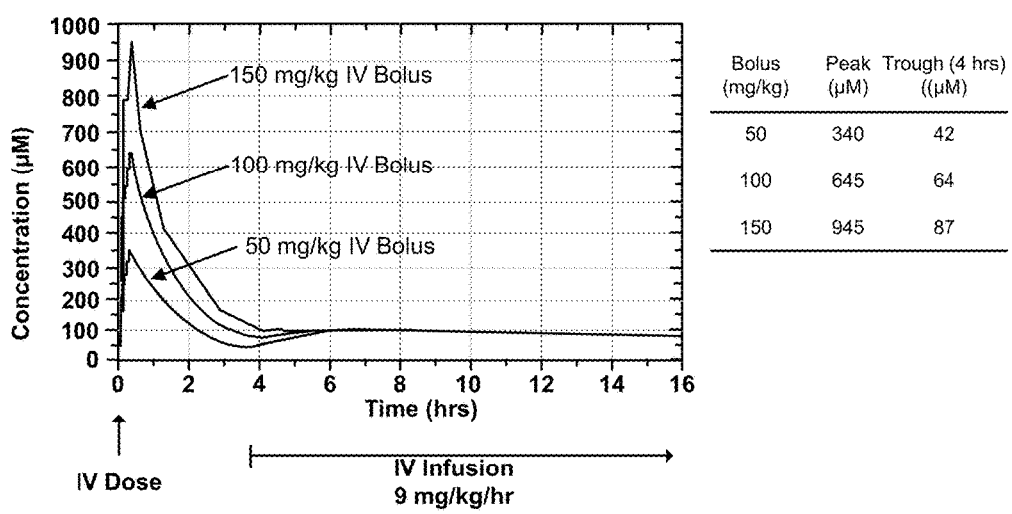
FIG. 13 depicts the plasma citrulline levels in patients administered a dose of citrulline (50, 100, or 150 mg/kg) postoperatively combined with an intravenous infusion of citrulline (9 mg/kg/hour) over 16 hours.

However, from the data above it was also determined that the ½ life of the bolus doses of IV citrulline was approximately 60-90 minutes and would require at least 4 hour dosing which is impractical even in an ICU setting. The pharmacokinteic modeling suggested a sustained citrulline level of approximately 100 µmol/L could be achieved by a bolus dose of 150 mg/kg of IV citrulline given at the beginning of surgery after initiation of cardiopulmonary bypass followed 4 hours later by a continuous infusion of 9 mg/kg/hr. The PK modeling of this regimen is shown in FIG. 13.

Figure 14A:
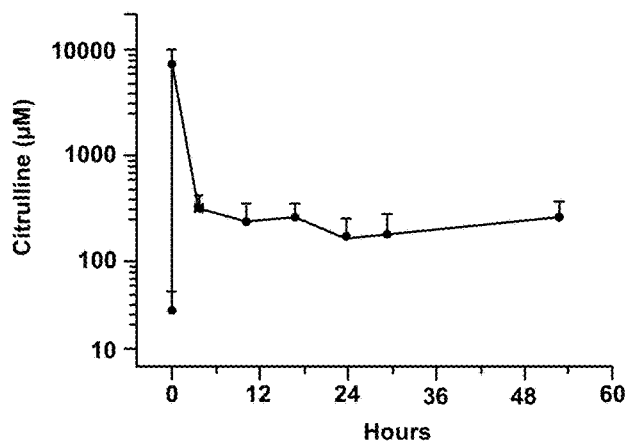
FIG. 14A depicts the mean citrulline levels in infants over 60 hours.
Figure 14B:
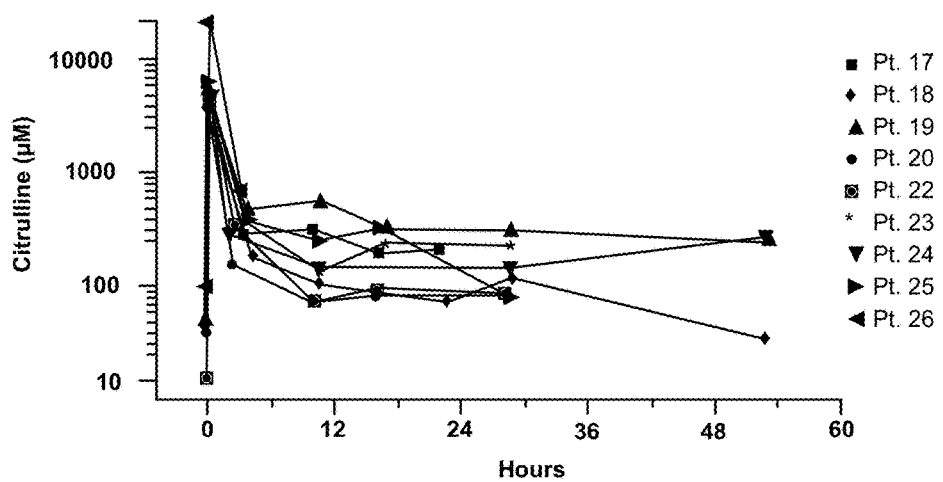
FIG. 14B depicts the citrulline levels of nine individual infants over 60 hours.
Figure 15:
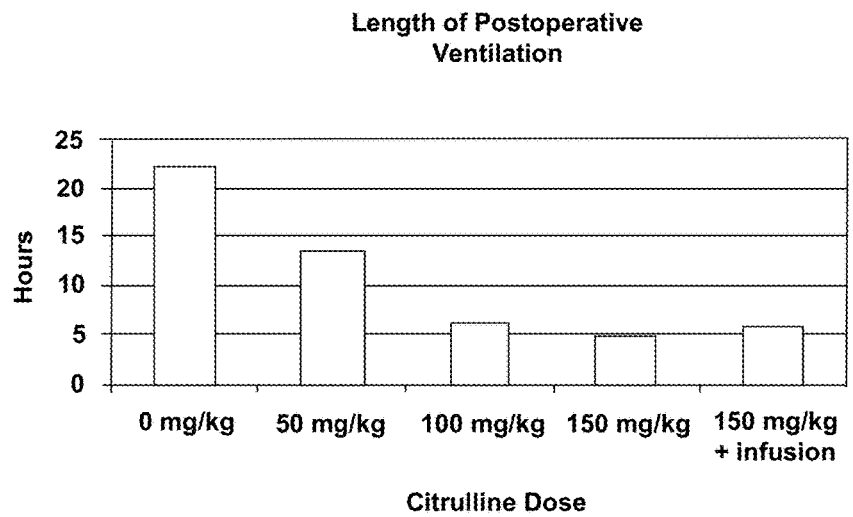
FIG. 15 depicts the length of postoperative ventilation with different doses of citrulline.

Patients were then enrolled using this revised protocol of a combination of a bolus dose of 150 mg/kg in the OR on CPB and a continuous infusion of 9 mg/kg/hr started postop in the PICU at 4 hours after the initial bolus dose. Citrulline data is available from 9 patients and are presented in FIGS. 14A-B.

Example 7

Intravenous Citrulline Study

An intravenous citrulline study conducted was a randomized, placebo controlled, double blind study with the primary clinical outcome being length of mechanical ventilation postoperatively and secondarily the incidence of postoperative pulmonary hypertension between the 2 treatment groups (citrulline vs placebo).

A total of 77 patients were enrolled at Vanderbilt Children's Hospital. Patients were screened based on the surgical schedule. Based on this schedule, patients undergoing one of the 5 planned cardiac surgeries included in this study were screened (patients undergoing the Norwood procedure are now excluded at the recommendation of the DSMB).

The study was stopped in preparation for a larger multi-center randomized placebo controlled trial. The analysis of the data from these 77 patients revealed that a majority who received citrulline did not reach the therapeutic sustained target plasma citrulline level of 100 µmol/L primarily due to removal of citrulline by hemofiltration occurring during cardiopulmonary bypass. These hemofiltration techniques had changed during the study, and the investigators were not aware of these changes.

Example 8

Protocol for Administration of Citrulline for Cardiac Surgery

The original pharmacokinetic model presumed a closed system. In the absence of significant metabolism and urine output during surgery, the model presumed that the therapeutic levels achieved by the original citrulline bolus would be maintained for the duration of surgery. However, at an unknown point early in the course of the study, perfusion practice changed to incorporate aggressive ultrafiltration and crystalloid exchange throughout surgery. This meant that the ultrafiltration effectively removed the citrulline from the circulation such that upon review of citrulline levels, virtually no patients had achieved therapeutic drug levels.

The study in this example was undertaken to test a revised dosing protocol designed to achieve and maintain therapeutic citrulline levels in the face of ultrafiltration and crystalloid replacement. While this pharmacokinetic endpoint was apparently achieved, the focus of this data presentation is upon the efficacy parameters that were assessed as secondary endpoints. The study recruited 22 patients randomized in equal numbers of 11 patients each to placebo and citrulline arms.

Results

Figure 16:
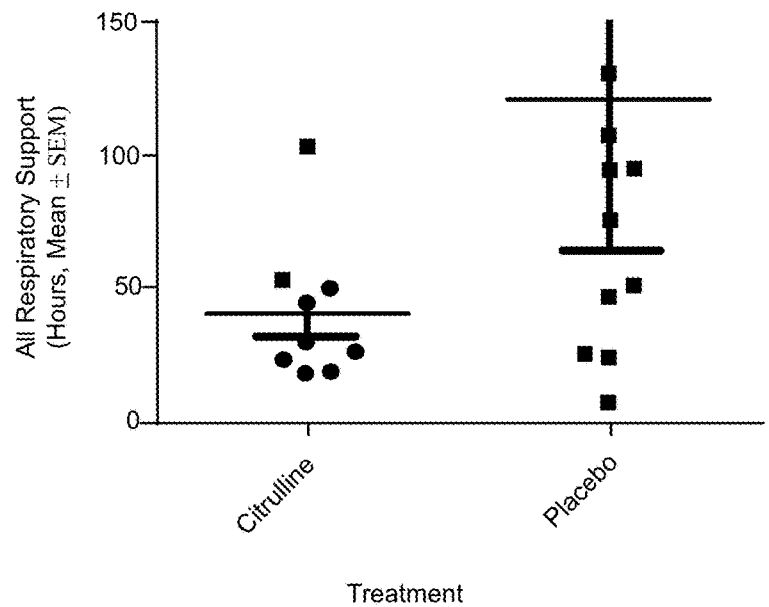
FIG. 16 depicts the effect of citrulline on respiratory outcome in congenital heart repair surgery.

Early in the course of the study, it was recognized that one of the two participating centers routinely extubated all patients in the operating room immediately following cessation of cardiopulmonary bypass. This precluded use of the duration of mechanical ventilation as an endpoint. Instead, a post-hoc analysis was applied using the duration of all forms of ventilatory support as a possible endpoint. FIG. 16 shows the placebo control group to have a roughly bimodal distribution of ventilator times, with some children remaining on respiratory support for extended periods of time. In contrast, the citrulline-treated children, with the exception of one outlier, showed a unimodal distribution with reduced durations of respiratory support. See FIG. 16. The differences between placebo and citrulline groups did not achieve significance but showed a strong trend when a Satterthwaite test was applied. In contrast, contingency table analysis, shown in Table 5, did achieve borderline significance. Overall, the results are considered to represent a strong trend.

TABLE 5

Contingency Table Analysis of Effects of Citrulline upon Duration of Respiratory Support

| Duration of Respiratory Support | Placebo | Citrulline |
| --- | --- | --- |
| ≤50 hours | 3 | 7 |
| >50 hours | 8 | 2 |

Figure 17:
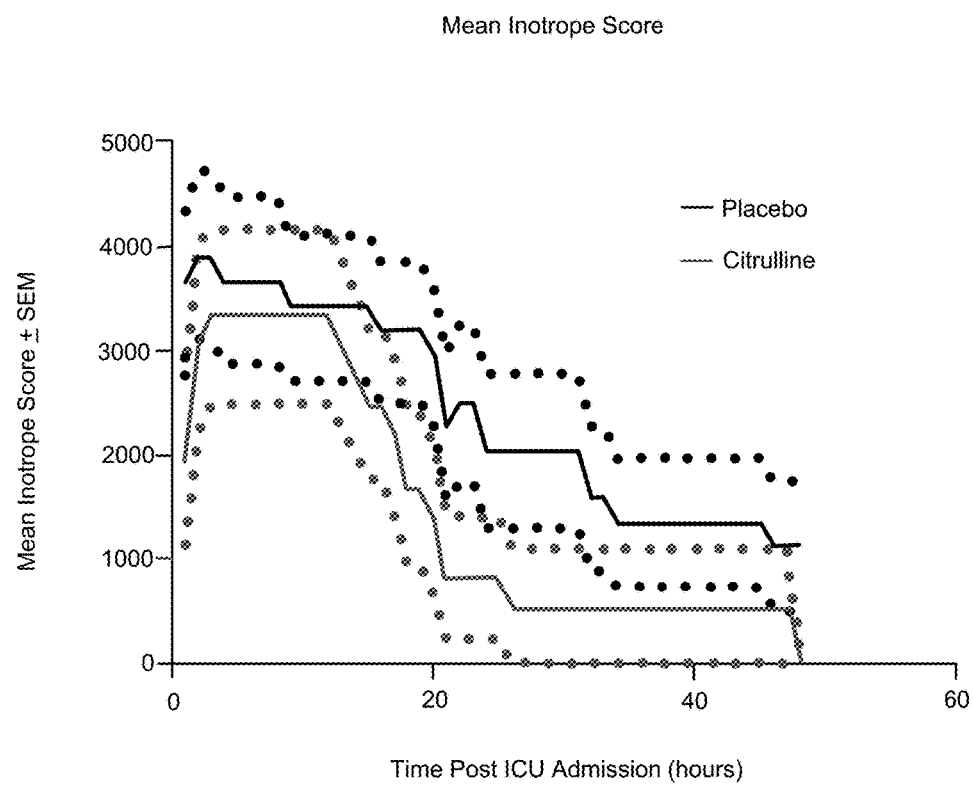
FIG. 17 depicts the mean Inotrope score of patents treated receiving citrulline (citrulline) versus those without citrulline (placebo).
Figure 18A:
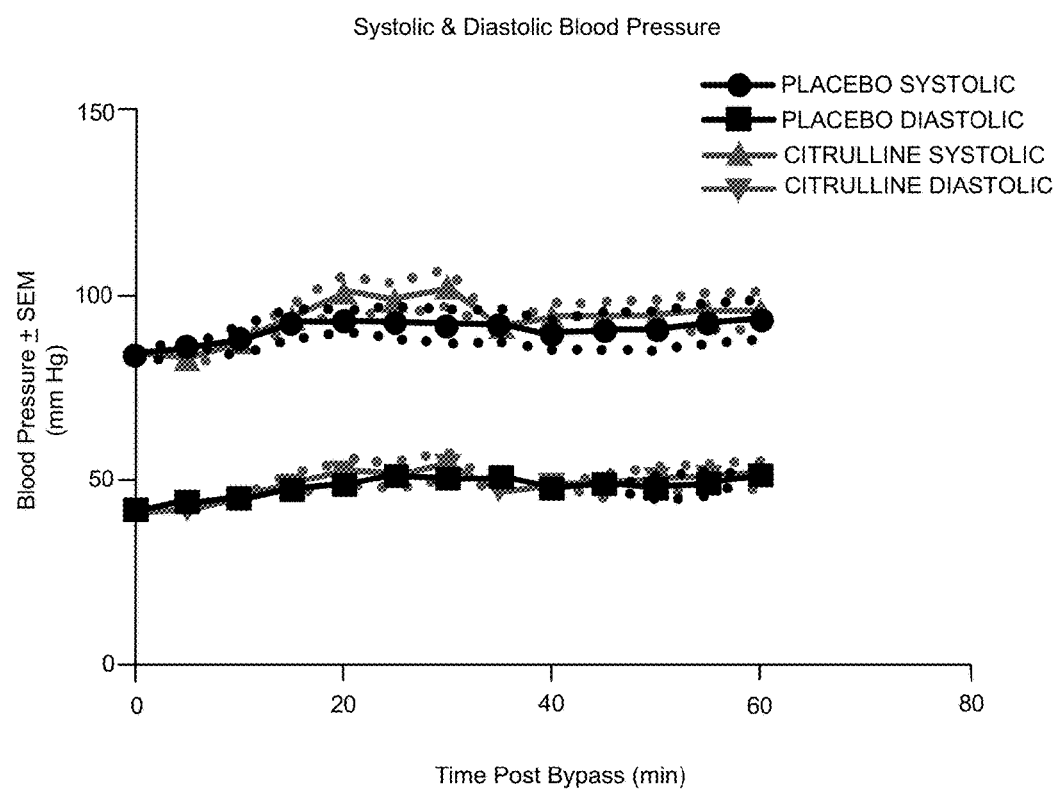
FIG. 18A depicts the systolic and diastolic blood pressure of patients receiving citrulline (citrulline) versus those without citrulline (placebo). No significant change in systolic and diastolic blood pressure of patients receiving citrulline.
Figure 18B:
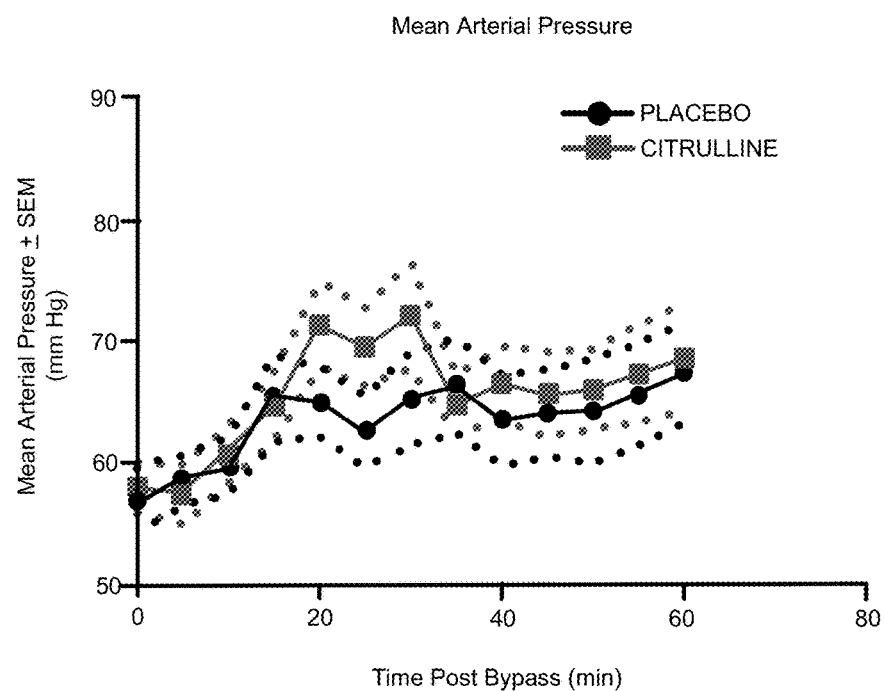
FIG. 18B depicts the mean arterial pressure of patients receiving citrulline (citrulline) versus those without citrulline (placebo). No significant change in the mean arterial pressure of patients receiving citrulline.

The cardiovascular parameters provide additional insights. FIG. 17 shows that the citrulline patients unexpectedly showed markedly better inotrope scores, particularly from 15 to 18 hours onward following ICU admission. Systolic blood pressure showed a mild transient elevation in the citrulline group commencing around 20 hours after cessation of bypass, while diastolic pressures were essentially identical between the two groups. FIG. 18A. Mean arterial pressure showed a slight transient increase in the citrulline group, as shown in FIG. 18B, reflective of the systolic pressure change. Given the transient nature of the systolic blood pressure elevation and arterial pressure elevation, the systolic pressure increase suggests a possible lesser need for inotropes than would be expected.

Duration of total respiratory support appears to be a viable endpoint for the study of citrulline to prevent acute pulmonary hypertension complicating congenital heart surgery repair. No adverse effects upon hemodynamic parameters were observed.

Example 9

Citrulline Formulation

Sterile citrulline may be produced first as a non-sterile bulk powder utilizing a process of bacterial (*Streptococcus faecalis*) fermentation of arginine followed by separation and extraction steps. The non-sterile bulk powder is then reconstituted and undergoes endotoxin reduction and sterile filtration steps followed by crystallization, drying, and micronization in an aseptic environment. The sterile bulk powder is then used as the "raw material" for aseptic filling into glass vials to produce the finished drug product which is reconstituted with a sterile diluent prior to use.

Each sterile vial of citrulline for injection may contain about 300 mg of sterile citrulline powder. Each vial may be reconstituted with 6 mL sterile water for injection, USP and is further diluted with about 5.9 mL of sodium chloride 0.9%, USP to equal a volume of 12 mL and a concentration of 300 mg/12 mL=25 mg/1 mL. Exemplary patient infusions may be in sodium chloride 0.9% USP to be administered at a concentration of about 25 mg/mL.

Example 10

Pharmacokinetics (Pk) and Safety of IV L-Citrulline Administration to Children and Infants Undergoing Cardiopulmonary Bypass (Cpb) for Surgical Repair of Congenital Heart Defects A multicenter, Phase IB single-blind, randomized, placebo controlled study was conducted to determine the pharmacokinetics (PK) and safety of IV L-citrulline administration to children and infants undergoing cardiopulmonary bypass (CPB) for surgical repair of congenital heart defects.

The primary objective of the study was to determine if a revised protocol of intravenous (IV) L-citrulline delivery given peri-operatively achieved a plasma citrulline level of >100 µmol/L in the group given citrulline and to compare that to citrulline levels in the placebo group, during follow-up in children undergoing surgical repair of an atrial septal defect (ASD) and/or a ventricular septal defect (VSD) or a partial or complete atrioventricular septal defect (AVSD).

Safety objectives were to further analyze the safety profile of citrulline and secondary objectives were to establish the impact of citrulline on postoperative clinical outcomes.

Twenty two (22) patients were enrolled and treated. The patients received study drug or placebo infusion according to a fixed dosing protocol starting at the initiation of CPB until 48 hours postoperatively or until removal of the arterial line. Study participation ended at discharge or at Day 28 whichever came first. The dosing regimen was designed to maintain plasma citrulline levels in the face of extended hemofiltration.

Plasma citrulline concentration levels were the primary PK variable; these were assessed in blood samples collected at 7 perioperative time points. Secondary PK variables were concentrations of arginine and nitric oxide (NO) metabolites in the same sample set. PK values were compared between groups.

Subjects received an IV citrulline bolus of 150 mg/kg or placebo at the initiation of CPB, followed by the addition of L-citrulline at a concentration of 200 µmol/L or placebo to the filtration or hemoconcentration replacement fluid used during CPB. A citrulline bolus of 20 mg/kg was administered 30 minutes after decannulation from CPB, immediately followed by a 9-mg/kg/hr continuous infusion of citrulline or placebo for 48 hours.

Primary safety assessments included hemodynamic monitoring to identify clinically significant hypotension using age-specific limits. Adverse event information was collected, and postoperative bleeding was recorded.

Further safety, laboratory, and clinical assessments were performed from baseline to discharge, secondary clinical variables included: postoperative mechanical ventilation, duration of total respiratory support, hemodynamic improvement, postoperative PVT by echocardiogram, serum creatinine and liver enzymes, inotrope score, duration of chest tube usage, length of intensive care unit stay, length of hospitalization and survival.

Figure 19:
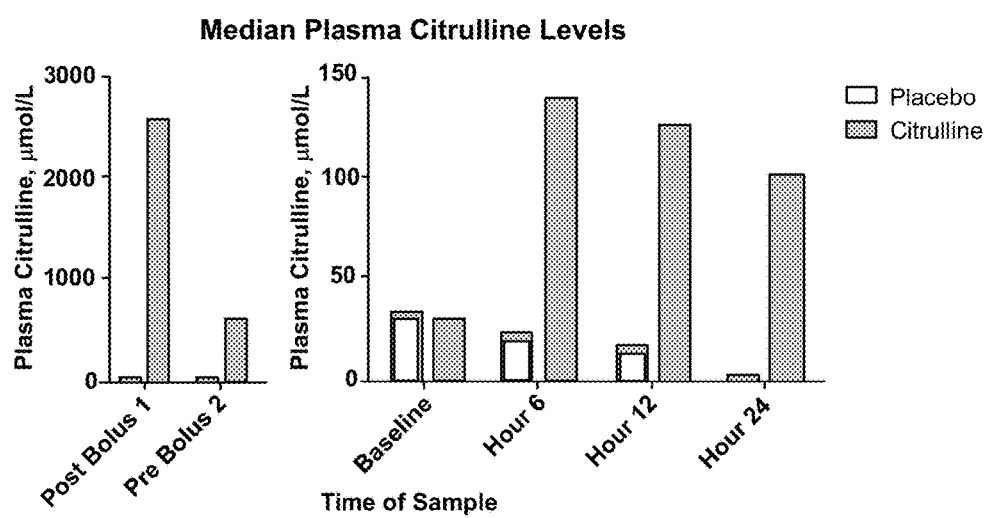
FIG. 19 depicts the median plasma citrulline levels in patients receiving pre-operative bolus, peri-operative, and post-operative citrulline.
Figure 20:
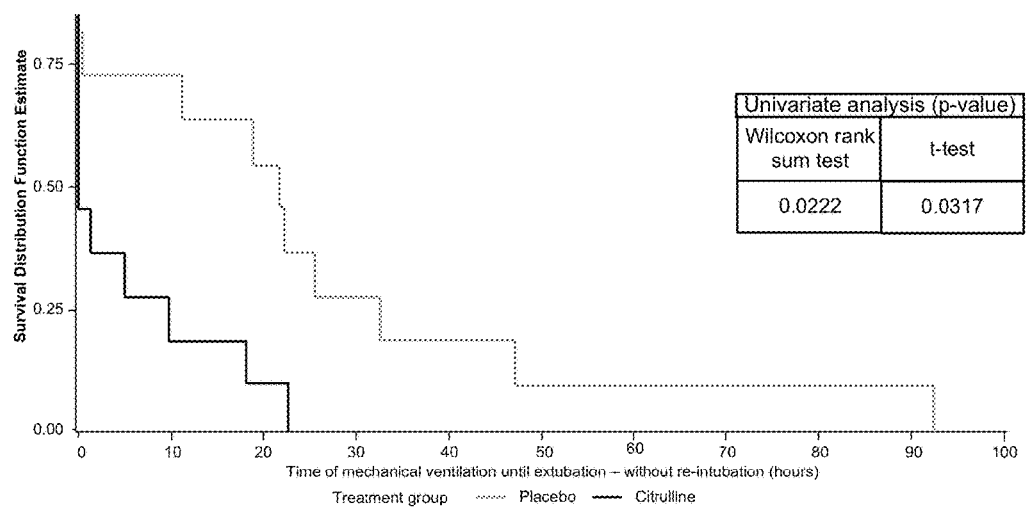
FIG. 20 Kaplan-Meier survival analysis of the duration of invasive mechanical ventilation from end of surgery until last extubation. (Excluding Re-intubation, censored). Patients receiving citrulline showed a reduced duration of mechanical ventilation. The differences in mechanical ventilation were statistically significant by the Wilcoxon rank sum test (p=0.0222) and by the ANOVA t-test (p=0.0317).

Analysis of the study results, is presently in its final stages but not all quality control has not been completed, meaning that the data that follows may be subject to minor change. Notwithstanding, the analyses, detailed below, showed the following as either preferable to use a composite variable comprised of the longer of the durations of each of these parameters as a surrogate for the duration of stay in the intensive care unit. The reason for this preference is that the actual duration of ICU stay may be influenced by extraneous variables such as time of day and bed availability, among others. Patients receiving study drug showed shorter composite durations of mechanical ventilation and inotrope therapy than did patients receiving placebo. Thus, as assessed by the composite surrogate marker variable, patients receiving study drug were ready for discharge from the ICU sooner than patients receiving placebo. The revised dosing protocol achieved plasma citrulline levels consistently above the target level of 100 µmol/L as shown below in FIG. 19. Patients receiving citrulline showed a reduced duration of mechanical ventilation as shown in FIG. 20.

Some differences were noted in clinical practice among sites with regard to mechanical ventilation. One site tended to extubated patients in the operating room without recording a time of extubation for such patients. For purposes of analysis, the duration of postoperative mechanical ventilation was set to zero for such patients. When these patients were stratified by treatment, it was shown that all 6 patients (100%) receiving i.v. L-citrulline had been extubated in the operating room, in comparison to only 2 of 6 patients (33%) in the placebo group.

Figure 21:
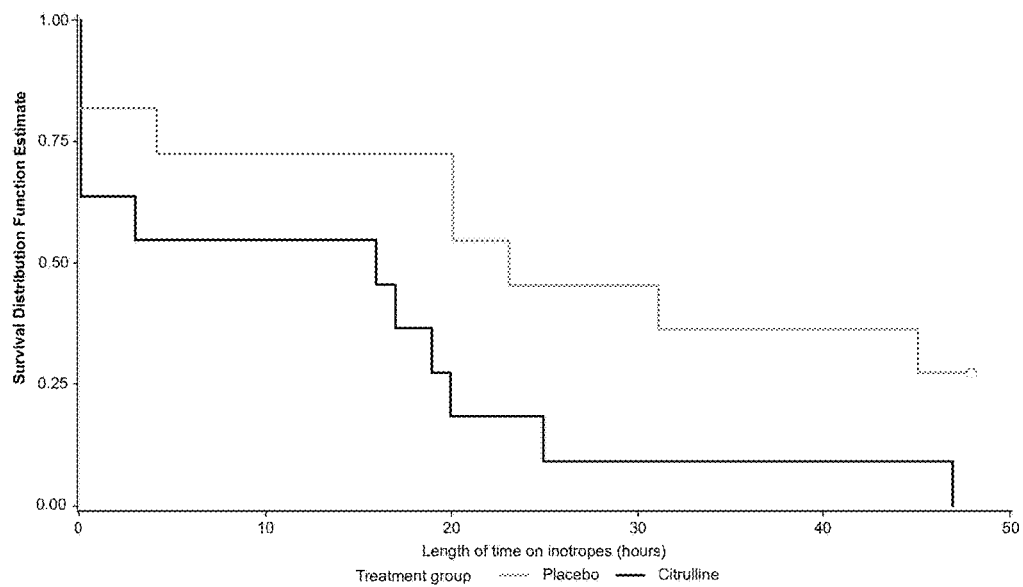
FIG. 21 depicts a Kaplan-Meier survival analysis of the length of time on inotropes. Univariate analysis (p-value): Wilcoxon rank sum test (0.0727); T-test (0.097).

As with the length of time of mechanical ventilation, the duration of inotrope therapy showed marked differences between the two treatment groups as shown in FIG. 21.

In FIG. 21, data are defined as the time between the start and end times of inotrope use. All missing or 0 total inotrope scores prior to the first measured score are set to 0 and are therefore not considered as being on inotropes. The total inotrope score is considered, which is calculated on the basis of Dopamine, Dobutamine, Milrinone, Epinephrine, Phenylephrine, and Norepinephrine. The length of time on inotropes of patients with no use of inotropes is set to 0 hours (not censored).

Figure 22:
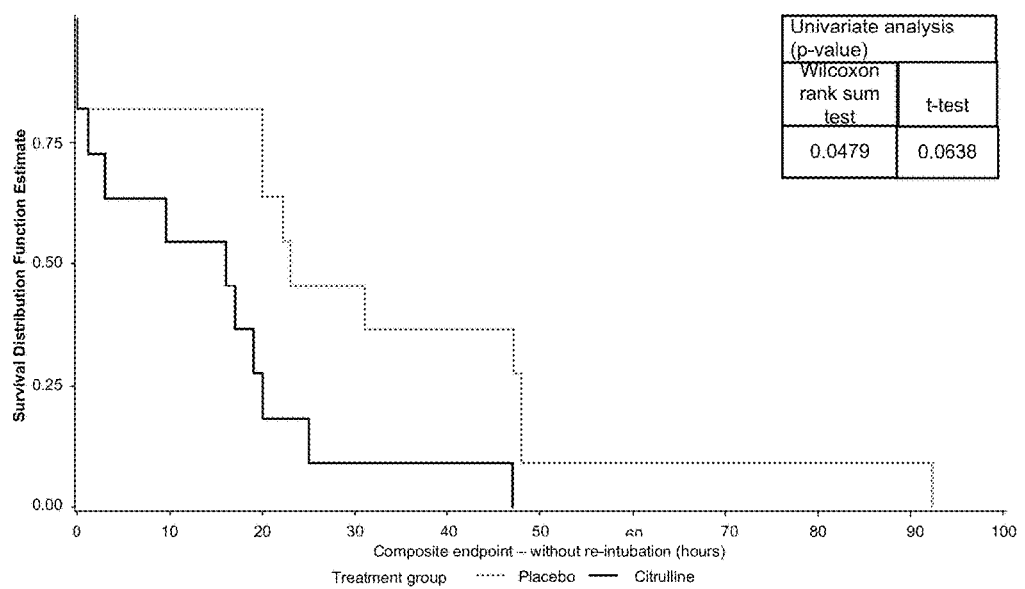
FIG. 22 depicts a Kaplan-Meier survival analysis of the length of time on inotropes. Univariate analysis (p-value): Wilcoxon rank sum test (0.0727); T-test (0.0987).

As previously mentioned, cessation of mechanical ventilation and of inotrope therapy are the two principal determinants of readiness for discharge from the intensive care unit. A composite variable comprising (for each subject) of the longer of the two parameters—duration of mechanical ventilation or of inotrope therapy—can serve as an effective and accurate surrogate for the duration of intensive care unit stay. FIG. 22 shows the differences in the composite variable when citrulline and placebo groups are compared. Patients receiving study drug showed shorter composite durations of mechanical ventilation and inotrope therapy than did patients receiving placebo. Thus, as assessed by the composite surrogate marker variable, patients receiving study drug were ready for discharge from the PICU sooner than patients receiving placebo. In addition to indicating shorter PICU time, shorter mechanical ventilation time lowers the added risk of physical injury.

In addition to achieving the targeted plasma citrulline levels, this study also yielded statistically significant and near significant results demonstrating citrulline treatment-dependent differences in the duration of mechanical ventilation and inotrope therapy between the treated and control groups in a small group of 22 subjects.

The duration of postoperative invasive mechanical ventilation was derived as the time in hours from separation from cardiopulmonary bypass until endotracheal extubation. If a patient required reintubation within 24 hours after extubation, the reintubation time was added in the main analysis. In a second analysis, the reintubation time was not included.

Including the reintubation time, the mean duration of invasive mechanical ventilation was clearly longer in the placebo group than in the citrulline treatment group, with citrulline-treated patients needing only an average of 5 hours of invasive ventilation while placebo-treated patients needed 37 hours. The difference did not reach statistical significance in the ANOVA test, most likely based on the large variation of durations in the placebo group. However, when the reintubation time was excluded, the difference between the group was still eminent and statistical significance was reached in the ANOVA (p=0.0317). Statistical significance for both analyses was shown by the Wilcoxon rank-sum test. See FIGS. 20-22.

Cessation of positive pressure ventilation and inotrope therapy are the two principal determinants of readiness for discharge from the intensive care unit. Together, as a composite variable comprised of the longer of the duration of positive pressure ventilatory support or of inotrope therapy, they can serve as an effective surrogate for the duration of intensive care unit stay. This latter variable is subject to confounding factors that may adventitiously prolong it, such as lack of bed availability.

In summary, the data from this study shows that the administered dosing regimen achieved the pharmacokinetic endpoint. Further, despite the extremely small sample size of the study, this study demonstrated clear treatment-dependent differences in favor of L-citrulline for the duration of mechanical ventilation and inotrope therapy between the treated and control groups. Combined in a composite variable, the results show clinically meaningful therapeutic efficacy for citrulline for the time to discharge from the intensive care unit. Thus, the results of this study indicate that IV citrulline treatment can play a beneficial role in preventing the clinical sequelae of CPB-induced lung injury.

While the foregoing invention has been described in connection with this preferred embodiment, it is not to be limited thereby but is to be limited solely by the scope of the claims which follow.

What is claimed is:

1. A method for maintaining pulmonary vascular tone in a patient undergoing cardiopulmonary bypass surgery for a cardiac defect, wherein the cardiopulmonary bypass surgery utilizes filtration, the method comprising:
   (a) administering about 100-300 mg/kg citrulline to the patient at the initiation of the surgery;
   (b) administering about 100-300 µmol/L citrulline to the patient via the hemoconcentration replacement fluid during the surgery;
   (c) administering a citrulline bolus of about 10-30 mg/kg about 15-45 minutes after decannulation from cardiopulmonary bypass, and,
   (d) infusing citrulline into the patient after the surgery for about 6-48 hours at about 5-15 mg/kg/hour,
       wherein the patient's plasma citrulline level is raised above 100 µmol/L.

2. The method of claim 1, wherein the cardiac defect is associated with excess pulmonary blood flow, atrial septal defect, large arterial septal defect, ventricular septal defect, large unrestrictive ventricular septal defect, single ventricle lesion, partial atrioventricular septal defect, complete atrioventricular septal defect, or ostium primum atrial septal defect.

3. The method of claim 1, wherein the surgery comprises an arterial switch procedure or Glenn and Fontan procedures.

4. The method of claim 1, wherein the bolus of citrulline at the initiation of the surgery in step (a) is about 150 mg/kg of citrulline.

5. The method of claim 1, wherein the citrulline in step (b) is added at about 200 µmol/L.

6. The method of claim 1, wherein the citrulline bolus is administered about 30 minutes after the surgery.

7. The method of claim 1, wherein the citrulline bolus in step (c) is about 20 mg/kg citrulline.

8. The method of claim 1, wherein a citrulline bolus in step (c) is administered about 30 minutes after decannulation from cardiopulmonary bypass.

9. The method of claim 1, wherein citrulline infusion in step (d) is infused into the patient for about 48 hours at about 9 mg/kg/hour.

10. The method of claim 1, wherein the patient is less than about 6 years old, less than 10 days old, at risk for persistent pulmonary hypertension (PPHN), at risk for acute lung injury, or a combination thereof.

11. The method of claim 1, wherein the patient's plasma citrulline level is raised to 100 µmol/L to 300 µmol/L for about 48 hours after surgery.

12. The method of claim 1, wherein the citrulline infusion is started within 5-10 minutes of the citrulline bolus in step (c).

13. The method of claim 1, wherein the surgery is completed within 4 hours as measured from completion of step (a) to initiation of step (d).

* * * * *